US011366093B2

(12) United States Patent
Viola et al.

(10) Patent No.: US 11,366,093 B2
(45) Date of Patent: Jun. 21, 2022

(54) DISPOSABLE SYSTEM FOR ANALYSIS OF HEMOSTATIC FUNCTION

(71) Applicant: HEMOSONICS, LLC, Charlottesville, VA (US)

(72) Inventors: Francesco Viola, Chapel Hill, NC (US); Timothy Higgins, Charlottesville, VA (US); Andrew Homyk, Charlottesville, VA (US); F. Scott Corey, Baltimore, MD (US); Franklin F. Regan, Charlottesville, VA (US); William F. Walker, Charlottesville, VA (US); David Bryant, Charlottesville, VA (US); Thomas Givens, Rougemont, NC (US); Cynthia Ann Lloyd, Durham, NC (US)

(73) Assignee: HEMOSONICS, LLC, Charlottesville, VA (US)

( * ) Notice: Subject to any disclaimer, the term of this patent is extended or adjusted under 35 U.S.C. 154(b) by 600 days.

(21) Appl. No.: 15/958,875

(22) Filed: Apr. 20, 2018

(65) Prior Publication Data
US 2018/0306774 A1    Oct. 25, 2018

Related U.S. Application Data

(60) Provisional application No. 62/488,045, filed on Apr. 20, 2017.

(51) Int. Cl.
*G01N 33/49* (2006.01)
*G01N 33/86* (2006.01)
*B01L 3/00* (2006.01)

(52) U.S. Cl.
CPC .......... *G01N 33/4905* (2013.01); *B01L 3/502* (2013.01); *G01N 33/86* (2013.01);
(Continued)

(58) Field of Classification Search
None
See application file for complete search history.

(56) References Cited

U.S. PATENT DOCUMENTS

| 4,112,740 A | 9/1978 | Brandestini |
| 4,558,589 A | 12/1985 | Hemmes et al. |

(Continued)

FOREIGN PATENT DOCUMENTS

| AU | 2011237383 | 7/2014 |
| CN | 1816306 | 8/2006 |

(Continued)

OTHER PUBLICATIONS

Jensen, Estimation of Blood Velocities Using Ultrasound, 1996, pp. 195-225.

(Continued)

*Primary Examiner* — Lore R Jarrett
(74) *Attorney, Agent, or Firm* — Meunier Carlin & Curfman LLC

(57) ABSTRACT

A disposable system, in some embodiments, includes a multi-channel or multi-chamber test cartridge device configured to operate with a testing system for evaluation of hemostasis in a subject by in vitro evaluation of a test sample from the subject. The disposable system, in some embodiments, is configured to interrogate the test sample to evaluate clot stiffness, strength, or other mechanical properties of the test sample to assess the function of various physiological processes occur during coagulation and/or dissolution of the resulting clot.

22 Claims, 20 Drawing Sheets

(52) U.S. Cl.
CPC .............. *B01L 2300/0825* (2013.01); *B01L 2300/0838* (2013.01)

(56) References Cited

U.S. PATENT DOCUMENTS

| | | | |
|---|---|---|---|
| 4,695,956 A | 9/1987 | Leveen et al. | |
| 4,705,756 A | 11/1987 | Spillert et al. | |
| 4,814,247 A | 3/1989 | Spillert et al. | |
| 4,849,340 A | 7/1989 | Oberhardt | |
| 4,852,577 A | 8/1989 | Smith et al. | |
| 4,900,679 A | 2/1990 | Spillert et al. | |
| 5,016,469 A | 5/1991 | Henderson | |
| 5,056,357 A | 10/1991 | Dymling et al. | |
| 5,104,975 A | 4/1992 | McCormick et al. | |
| 5,204,525 A | 4/1993 | Hillman et al. | |
| 5,205,159 A | 4/1993 | Carr, Jr. | |
| 5,234,839 A | 8/1993 | McCormick et al. | |
| 5,273,517 A | 12/1993 | Barone et al. | |
| 5,311,908 A | 5/1994 | Barone et al. | |
| 5,331,964 A | 7/1994 | Trahey et al. | |
| 5,473,536 A | 12/1995 | Wimmer | |
| 5,487,387 A | 1/1996 | Trahey et al. | |
| RE35,171 E | 3/1996 | McCormick et al. | |
| 5,504,011 A | 4/1996 | Gavin et al. | |
| 5,605,154 A | 2/1997 | Ries et al. | |
| 5,606,971 A | 3/1997 | Sarvazyan et al. | |
| 5,629,209 A | 5/1997 | Braun et al. | |
| 5,655,535 A | 8/1997 | Friemel et al. | |
| 5,657,760 A | 8/1997 | Ying et al. | |
| 5,673,699 A | 10/1997 | Trahey et al. | |
| 5,744,898 A | 4/1998 | Smith et al. | |
| 5,800,781 A | 9/1998 | Gavin et al. | |
| 5,810,731 A | 9/1998 | Sarvazyan et al. | |
| 5,854,423 A | 12/1998 | Venegas | |
| 5,888,826 A | 3/1999 | Ostgaard et al. | |
| 5,899,861 A | 5/1999 | Friemel et al. | |
| 5,921,928 A | 7/1999 | Greenleaf et al. | |
| 5,952,560 A | 9/1999 | Collings et al. | |
| 6,016,712 A | 1/2000 | Warden et al. | |
| 6,039,691 A | 3/2000 | Walker et al. | |
| 6,046,051 A | 4/2000 | Jina | |
| 6,083,159 A | 7/2000 | Driscoll, Jr. et al. | |
| 6,114,135 A | 9/2000 | Goldstein | |
| 6,117,081 A | 9/2000 | Jago et al. | |
| 6,135,957 A | 10/2000 | Cohen et al. | |
| 6,213,950 B1 | 4/2001 | Cespedes et al. | |
| 6,221,672 B1 | 4/2001 | Baugh et al. | |
| RE37,171 E | 5/2001 | Busche et al. | |
| 6,225,126 B1 | 5/2001 | Cohen et al. | |
| 6,232,127 B1 | 5/2001 | Lane et al. | |
| 6,264,609 B1 | 7/2001 | Herrington et al. | |
| 6,270,459 B1 | 8/2001 | Konofagou et al. | |
| 6,277,074 B1 | 8/2001 | Chaturvedi et al. | |
| 6,283,917 B1 | 9/2001 | Jago et al. | |
| 6,318,191 B1 | 11/2001 | Chen | |
| 6,371,912 B1 | 4/2002 | Nightinggale et al. | |
| 6,402,704 B1 | 6/2002 | McMorrow | |
| 6,412,344 B1 | 7/2002 | Danicich et al. | |
| 6,436,722 B1 | 8/2002 | Clark et al. | |
| 6,454,714 B1 | 9/2002 | Ng et al. | |
| 6,494,834 B2 | 12/2002 | Konofagou et al. | |
| 6,508,768 B1 | 1/2003 | Hall et al. | |
| 6,514,204 B2 | 2/2003 | Alam et al. | |
| 6,535,835 B1 | 3/2003 | Rubin et al. | |
| 6,537,819 B2 | 3/2003 | Cohen et al. | |
| 6,573,104 B2 | 6/2003 | Carr, Jr. et al. | |
| 6,613,286 B2 | 9/2003 | Braun et al. | |
| 6,613,573 B1 | 9/2003 | Cohen | |
| 6,632,678 B2 | 10/2003 | Aiken et al. | |
| 6,685,646 B2 | 2/2004 | Cespedes et al. | |
| 6,687,625 B2 | 2/2004 | Srinivasan et al. | |
| 6,692,439 B1 | 2/2004 | Walker et al. | |
| 6,716,168 B2 | 4/2004 | Nock et al. | |
| 6,726,629 B1 | 4/2004 | Frinking et al. | |
| 6,750,053 B1 | 6/2004 | Widrig Opalsky | |
| 6,764,448 B2 | 7/2004 | Trahey et al. | |
| 6,787,363 B2 | 9/2004 | Cohen et al. | |
| 6,797,519 B2 | 9/2004 | Cohen et al. | |
| 6,890,299 B2 | 5/2005 | Cohen et al. | |
| 6,951,544 B2 | 10/2005 | Trahey et al. | |
| 7,179,652 B2 | 2/2007 | Cohen et al. | |
| 7,192,726 B1 | 3/2007 | Carr, Jr. et al. | |
| 7,202,048 B2 | 4/2007 | Carr, Jr. | |
| 7,207,939 B2 | 4/2007 | Husher | |
| 7,247,488 B2 | 7/2007 | Ghai et al. | |
| 7,261,861 B2 | 8/2007 | Kautzky | |
| 7,374,538 B2 | 5/2008 | Nightingale et al. | |
| 7,399,637 B2 | 7/2008 | Wright et al. | |
| 7,422,905 B2 | 9/2008 | Clague et al. | |
| 7,439,069 B2 | 10/2008 | Nippoldt et al. | |
| 7,524,670 B2 | 4/2009 | Cohen et al. | |
| 7,674,616 B2 | 3/2010 | Farnam, III et al. | |
| 7,732,213 B2 | 6/2010 | Cohen et al. | |
| 7,892,188 B2 | 2/2011 | Walker et al. | |
| 7,912,661 B2 | 3/2011 | Zeng | |
| 7,972,271 B2 | 7/2011 | Johnson et al. | |
| 8,058,023 B2 | 11/2011 | Gurbel | |
| 8,372,343 B2 | 2/2013 | Goldstein | |
| 8,548,759 B2 | 10/2013 | Walker et al. | |
| 8,740,818 B2 | 6/2014 | Walker et al. | |
| 9,031,701 B2 | 5/2015 | Viola et al. | |
| 9,272,280 B2 | 3/2016 | Viola et al. | |
| 9,410,971 B2 | 8/2016 | Viola et al. | |
| 9,977,039 B2 | 5/2018 | Viola et al. | |
| 2002/0013530 A1 | 1/2002 | Cespedes et al. | |
| 2002/0040187 A1 | 4/2002 | Alam et al. | |
| 2002/0081741 A1 | 6/2002 | Braun et al. | |
| 2003/0013958 A1 | 1/2003 | Govari et al. | |
| 2003/0073244 A1 | 4/2003 | Cohen et al. | |
| 2003/0105398 A1 | 6/2003 | Vitek | |
| 2003/0113929 A1 | 6/2003 | Baugh et al. | |
| 2003/0170883 A1 | 9/2003 | Martin et al. | |
| 2003/0171676 A1 | 9/2003 | Trahey et al. | |
| 2003/0199082 A1 | 10/2003 | Miller | |
| 2003/0204141 A1 | 10/2003 | Nock et al. | |
| 2004/0065143 A1 | 4/2004 | Husher | |
| 2004/0068184 A1 | 4/2004 | Trahey et al. | |
| 2004/0072357 A1 | 4/2004 | Stiene et al. | |
| 2004/0076546 A1 | 4/2004 | Bissett | |
| 2004/0088317 A1 | 5/2004 | Fabrick et al. | |
| 2004/0167403 A1 | 8/2004 | Nightingale et al. | |
| 2004/0203163 A1 | 10/2004 | Cohen et al. | |
| 2004/0214337 A1 | 10/2004 | Kautzky | |
| 2005/0004463 A1 | 1/2005 | Chen et al. | |
| 2005/0015001 A1 | 1/2005 | Lec et al. | |
| 2005/0053305 A1 | 3/2005 | Li et al. | |
| 2005/0148899 A1 | 7/2005 | Walker et al. | |
| 2005/0164373 A1 | 7/2005 | Oldham et al. | |
| 2005/0215901 A1 | 9/2005 | Anderson et al. | |
| 2005/0216987 P1 | 9/2005 | Murakami | |
| 2007/0038095 A1 | 2/2007 | Greenleaf et al. | |
| 2007/0059840 A1 | 3/2007 | Cohen et al. | |
| 2007/0078631 A1 | 4/2007 | Ariyoshi et al. | |
| 2007/0184508 A1 | 8/2007 | Cohen et al. | |
| 2007/0266778 A1 | 11/2007 | Corey et al. | |
| 2007/0276236 A1 | 11/2007 | Jong | |
| 2008/0038828 A1 | 2/2008 | Cohen et al. | |
| 2008/0194967 A1 | 8/2008 | Sliwa et al. | |
| 2008/0200343 A1 | 8/2008 | Clemens | |
| 2008/0249408 A1 | 10/2008 | Palmeri et al. | |
| 2008/0261261 A1 | 10/2008 | Grimes et al. | |
| 2008/0280285 A1* | 11/2008 | Chen ............... B01L 3/502715 435/5 |
| 2008/0297169 A1 | 12/2008 | Greenquist et al. | |
| 2009/0112483 A1 | 4/2009 | Cohen | |
| 2009/0269837 A1 | 10/2009 | Shevkoplyas et al. | |
| 2009/0286692 A1* | 11/2009 | Wainwright ...... B01L 3/502723 506/9 |
| 2010/0154520 A1 | 6/2010 | Schubert | |
| 2010/0190193 A1 | 7/2010 | Calatzis et al. | |
| 2010/0274130 A1 | 10/2010 | Anand et al. | |
| 2011/0034805 A1 | 2/2011 | Walker et al. | |
| 2011/0151491 A1 | 6/2011 | Dennis et al. | |
| 2011/0172661 A1 | 7/2011 | Designer et al. | |

(56) References Cited

U.S. PATENT DOCUMENTS

| | | | |
|---|---|---|---|
| 2011/0252352 A1 | 10/2011 | Viola et al. | |
| 2012/0232803 A1* | 9/2012 | Viola | G01N 29/032 702/19 |
| 2012/0244392 A1 | 9/2012 | Kleiman | |
| 2012/0252127 A1 | 10/2012 | Bansil et al. | |
| 2012/0294767 A1 | 11/2012 | Viola et al. | |
| 2012/0329082 A1* | 12/2012 | Viola | G01N 29/024 435/13 |
| 2013/0190584 A1 | 7/2013 | Walker et al. | |
| 2016/0139080 A1 | 5/2016 | Viola et al. | |
| 2016/0274067 A1 | 9/2016 | Walker et al. | |
| 2016/0313357 A1 | 10/2016 | Viola et al. | |

FOREIGN PATENT DOCUMENTS

| | | |
|---|---|---|
| CN | 101035479 | 9/2007 |
| CN | 103649751 A | 3/2014 |
| DE | 20 2014 002289 U1 | 9/2014 |
| EP | 1162457 | 12/2001 |
| EP | 1347058 | 9/2003 |
| EP | 1901065 | 3/2008 |
| EP | 2555704 | 2/2013 |
| EP | 3001196 A2 | 3/2016 |
| WO | 2002/050535 A1 | 6/2002 |
| WO | 2008093216 | 8/2008 |
| WO | 2009152094 | 12/2009 |
| WO | 2011035162 | 3/2011 |
| WO | 2011127436 | 10/2011 |
| WO | 2012159021 | 2/2012 |
| WO | 2013105987 | 10/2013 |
| WO | 2015184433 | 12/2015 |

OTHER PUBLICATIONS

Office Action received in U.S. Appl. No. 15/357,492, dated Jun. 22, 2017.
Amukele, et al., "Comparison of plasma with whole blood prothrombin time and fibrinogen on the same instrument," American Journal of Clinical Pathology, vol. 133, No. 4, Apr. 2010, pp. 550-556.
Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.
Anderson, "Preventing Deep Vein Thrombosis and Pulmonary Embolism," Center for Outcomes Research, U Mass Med Center, 1998, 23 pages.
Becker, R., "Cell-based models of coagulation: a paradigm in evolution," Journal of Thrombosis and Thrombolysis, vol. 20, No. 1, Aug. 2005, pp. 65-68.
Beer: Center for Reproductive Immunology & Genetics, "Thrombophilia: Inherited and Acquired," 6 pages, http://repro-med.net/papers/thromb.php. Mar. 30, 2005.
Bell, et al., "Thrombelastographic evaluation of coagulation in transurethral prostatectomy," British Journal of Urology, vol. 78, No. 5, 1996, pp. 737-741.
Bercoff et al., "In vivo breast tumor detection using transient elastography," Ultrasound in Medicine & Biology, vol. 29, No. 10, 2003, pp. 1387-1396.
Bercoff, et al., "Supersonic Shear Imaging: A New Technique for Soft Tissue Elasticity Mapping," IEEE Transactions on Ultrasonics Ferroelectrics & Frequency Control, vol. 51, No. 4, 2004, pp. 396-409.
Bilgen, et al., "Error analysis in acoustic elastography. II. Strain estimation and SNR analysis", Journal of the Acoustical Society of America, vol. 101, 1997, pp. 1147-1154.
Bohs, et al., "A Real Time System for Quantifying and Displaying Two-Dimensional Velocities using Ultrasound," Ultrasound in Medicine & Biology, vol. 19, No. 9, Jul. 1993, pp. 751-761.
Bombeli, et al., "Updates in perioperative coagulation: physiology and management of thromboembolism and haemorrhage," British Journal of Anaesthesia; vol. 93, No. 2, Aug. 2004, pp. 275-287.

Bonnefous, et al., "Time Domain Formulation of Pulse-Doppler Ultrasound and Blood Velocity Estimation by Cross Correlation," Ultrasonic Imaging 8, 1986, pp. 73-85.
Brock, et al., "Assessing Thrombin Generation at the Point of Care," Clinical Chemistry, vol. 55, No. 3, Mar. 2009, pp. 398-399.
Carr, M., "In vitro assessment of platelet function," Transfusion of Medicine Reviews, vol. 11, No. 2, Apr. 1997, pp. 106-115.
Carroll, et al., "Measurement of functional fibrinogen levels using the Thrombelastograph," Journal of Clinical Anesthesia, vol. 20, No. 3, May 2008, pp. 186-190.
Carter, G., "Coherence and time delay estimation," Proc IEEE, vol. 75, No. 2, 1987, pp. 236-255.
Chakroun et al., "The influence of fibrin polymerization and platelet-mediated contractile forces on citrated whole blood thromboelastography profile," Thrombosis and Haemostasis, vol. 95, No. 5, May 2006, pp. 822-828.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.
Chavez, J., "A novel thrombelastograph tissue factor/kaolin assay of activated clotting times for monitoring heparin anticoagulation during cardiopulmonary bypass," Anesthesia and Analgesia; vol. 99, No. Nov. 5, 2004, pp. 1290-1294.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Curry, et al., "Convention and near-patient tests of coagulation," British Journal of Anaesthesia, vol. 7, No. 2, Apr. 2007, pp. 45-50.
Dahlback, B., "Blood Coagulation," Lancet, vol. 355, No. 9215, May 2000, pp. 1627-1632.
Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.
Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.
Emelianov et al., "Ultrasound Elasticity Imaging of Deep Venous Thrombosis," Proc. IEEE Ultrasonics Symp., 2000, pp. 1791-1794.
Evans, et al., "Rheometry and associated techniques for blood coagulation studies," Medical Engineering and Physics, vol. 30, No. 6, Jul. 2008, pp. 671-679.
Fatemi et al., "C-Scan Imaging by Radiation Force Stimulated Acoustic Emission Method," Proc. IEEE Ultrasonics Symp., 1996, pp. 1459-1462.
Fatemi, et al., "Application of radiation force in noncontact measurement of the elastic parameters," Ultrasonic Imaging, vol. 21, No. 2, Apr. 1999 pp. 147-154.
Fatemi, et al., "Ultrasound-Stimulated Vibro-Acoustic Spectography," Science Magazine, vol. 280, No. 5360, 1998, pp. 82-85.
Ferraris, et al., "2011 Update to The Society of Thoracic Surgeons and the Society of Cardiovascular Anesthesiologists Blood Conservation Clinical Practice Guidelines," Annals of Thoracic Surgery, vol. 91, 2011, pp. 944-982.
Fertner, et al., "Comparison of Various Time Delay Estimation Methods by Comptuer Simulation," IEEE Transactions on Acoustics, Speech, and Signal Processing, vol. 34, No. 5, 1986, pp. 1329-1330.

(56) References Cited

OTHER PUBLICATIONS

Flax, et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, Nov. 1988, pp. 758-767.

Freedman, et al., "A Meta-Analysis of Thromboembolic Prophylaxis Following Elective Total Hip Arthroplasty," Journal of Bone and Joint Surgery, vol. 82-A, 2000, pp. 929-938.

Gaetano, G. de, et al., "Effect of Platelets on Clot Structuration, a Thrombelastographic Study," Thrombosis Research, vol. 3, No. 4, pp. 425-435, 1973.

Ganter, et al., "Active, personalized, and balanced coagulation management saves lives in patients with massive bleeding," Anesthesiology, vol. 133, No. 5, Nov. 2010, pp. 1016-1018.

Gallippi, et al., "Adaptive clutter filtering via blind source," Ultrasonic Imaging, vol. 24, No. 4, 2002, pp. 193-214.

Gallippi, et al., "BSS-based filtering of physiological and ARFI-induced tissue and blood motion," Ultrasound in Medicine and Biology, vol. 29, No. 11, 2003, pp. 1583-1592.

Gallippi, et al., "Complex blind source separation for acoustic radiation force impulse imaging in the peripheral vasculature, in vivo," IEEE Ultrasonics Symposium, vol. 1, 2004, pp. 596-601.

Ganter, et al., "Coagulation monitoring: current techniques and clinical use of viscoelastic point-of-care coagulation devices," Anesthesia and Analgesia, vol. 106, No. 5, May 2008, pp. 1366-1375.

Gauss, et al., "Adaptive Imagining in the Thyroid Using Fundamental and Harmonic Echo Data," presented at IEEE Ultrasonics Symposium, 1999, pp. 1515-1519.

Gauss, et al., "Wavefront Estimation in the Human Breast," presented at SPIE Medical Imaging, vol. 4325, 2001, pp. 172-180.

Giunta, et al., "Estimation of Global Motion Parameters by Complex Linear Regression," IEEE Transactions on Image Processing, vol. 8, No. 11, 1999, pp. 1652-1657.

Glidden, Paul F., et al., "Thromboelastograph Assay for Measuring the Mechanical Strength of Fibrin Sealant Clots," Clinical and Applied Thombosis/Hemostasis, vol. 6, No. 4, Oct. 2000, pp. 226-233.

Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.

Greilich, Philip E., et al., "A Modified Thromboelastographic Method for Monitoring c7E3 Fab in Heparinized Patients," Anesth Analg, vol. 84, 1997, pp. 31-38.

Greilich, Philip E., et al., "Near-Site Monitoring of the Antiplatelet Drug Abciximad Using the Hemodyne Analyzer and Modified Thrombelastograph," Journal of Cardiothoracic and Vascular Anesthesis, vol. 13, No. 1, Feb. 1999, pp. 58-64.

Gurbel, et al., "Platelet function monitoring in patients with coronary artery disease," Journal of the American College of Cardiology, vol. 50, No. 19, Nov. 2007, pp. 1822-1834.

Hardisty R. M. et al, "Fibrinogen as a Co-factor in the Reaction of Platelets with Kaolin," May 7, 1966, Nature Publishing Group, Edition 210, vol. 644. Abstract (http://www.nature.com/nature/journal/v210/n5036/abs/210644a0.html).

Harris, et al., "Evaluation of recurrent thrombosis and hypercoagulability," American Family Physician, vol. 56, No. 6, Oct. 1997, pp. 1591-1596, pp. 1601-1602.

Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.

Hartley, et al., "Doppler Measurement of Acoustic Streaming," IEEE Ultrasonics Symposium Proceedings, 1995, pp. 1537-1540.

Hett, et al., "Sonoclot Analysis," British Journal of Anaesthesia, vol. 75, No. 6, Dec. 1995, pp. 771-776.

Hirsh, et al., "How we diagnose and treat deep vein thrombosis," Blood, vol. 99, 2002, pp. 3102-3110.

Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.

Hoffman, et al., "A cell-based model of hemostasis," Thrombosis and Haemostasis, vol. 85, No. 6, Jun. 2001, pp. 958-965.

Huang, et al., "Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.

Huang, et al., "Detection of blood coagulation and clot formation using quantitative ultrasonic parameters," Ultrasound in Medicine and Biology, vol. 31, No. 11, Nov. 2005, pp. 1567-1573.

Ickx, Brigitte, "Point-of-Care Monitoring of Haemostasis in the OR and the ICU," European Society of Anaesthesiologists. Jun. 5, 2004, pp. 79-83.

International Search Report and Written Opinion of the International Searching Authority, received in corresponding application PCT/US2010/049342, dated Nov. 16, 2010.

International Search Report and Written Opinion of the International Searching Authority, received in corresponding application PCT/US2011/031832, dated Dec. 15, 2011.

International Preliminary Report on Patentability and Written Opinion, dated Oct. 8, 2013, in connection with International Application No. PCT/US2012/025270.

International Search Report, dated Sep. 30, 2013, in connection with International Application No. PCT/US2012/025270.

International Preliminary Report on Patentability and Written Opinion, dated Aug. 27, 2013, in connection with International Application No. PCT/US2012/025278.

International Search Report, dated Aug. 20, 2013, in connection with International Application No. PCT/US2012/025278.

International Preliminary Report on Patentability and Written Opinion, dated Nov. 19, 2013, in connection with International Application No. PCT/US2012/038553.

International Search Report, dated Jan. 2, 2013, in connection with International Application No. PCT/US2012/038553.

International Preliminary Report on Patentability and Written Opinion, dated Oct. 9, 2012, in connection with International Application No. PCT/US2011/031832.

International Preliminary Report on Patentability and Written Opinion, dated Mar. 20, 2012, in connection with International Application No. PCT/US2010/049342.

Ivandic, et al., "Determination of clopidogrel resistance by whole blood platelet aggregometry and inhibitors of the P2Y12 receptor," Clinical Chemistry, vol. 52, No. 3, Mar. 2006, pp. 383-388.

Jacovitti, et al., "Discrete Time Techniques for Time Delay Estimation," IEEE Transactions on Signal Processing, vol. 41, No. 2, Feb. 1993, pp. 525-533.

Jensen, "A New Method for Estimation of Velocity Vectors," IEEE Transactions on Ultrasonics, Ferroelectrics and Frequency Control, vol. 45, No. 3, 1998, pp. 837-851.

Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.

Jolliffe, IT., "Principal Component Analysis," Springer Series in Statistics, 2nd edition, Springer, NY, 2002, pp. 1-8.

Kadi, et al., "On the performance of regression and step-initialized IIR Clutter Filters," IEEE Transactions on Ultrasonics, Ferroelectrics, and Frequency Control, vol. 42, 1995, pp. 827-837.

Kasai, et al., "Real-time Two-Dimensional Blood Flow Imaging Using an Autocorrelation Technique," IEEE Ultrasonics Symposium, vol. 32, No. 3, 1985, pp. 458-464.

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab-Modified Thrombelatography in Patients Undergoing Cardiac Surgery," Anesth Analg, vol. 89, 1999, pp. 580-584.

(56) References Cited

OTHER PUBLICATIONS

Khurana, Sandeep, et al., "Monitoring Platelet Glycoprotein IIb/IIa-fibrin Interaction with Tissue Factor-Activated Thromboelastography," J Lab Clin Med, vol. 130, No. 4, 1997, pp. 401-411.

Khurana, Sandeep, et al., "Thromboelastography Can Rapidly Bioassay Fibrinogen," Anesthesiology, vol. 85, No. 3A, Sep. 1996, p. A457.

Koepke, J., "Point-of-Care Coagulation Testing," Laboratory Medicine, vol. 31, No. 6, Jun. 2000, pp. 343-346.

Kruse, et al., "A new high-resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.

Ledoux, et al., "Reduction of the clutter component in Doppler ultrasound signals based on singular value decomposition: a simulation study," vol. 19, No. 1, 1997, pp. 1-18.

Lerner, et al., "Sono-elasticity: medical elasticity images derived from ultrasound signals in mechanically vibrated targets," Ultrasound in Medicine & Biology, vol. 16, 1998, pp. 317-327.

Libgot, R., et al., "High frequency ultrasound characterization of the blood clotting process: intra- and inter-individual variations," 2005 IEEE Ultrasonics Symposium, IEEE, vol. 4, 2005, pp. 2259-2262.

Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.

Mauldin, Jr., F.W., et al., "Adaptive Force Sonorheometry for Assessment of Whole Blood Coagulation," Clin Chim Acta, vol. 411, Issues 9-10, 2010, pp. 638-644.

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.

Nielson, er al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Oberhardt, et al., "Dry reagent technology for rapid, convenient measurements of blood coagulation and fibrinolysis," Clinical Chemistry, vol. 37, No. 4, Apr. 1991, pp. 520-526.

O'Donnell, et al., "Role of the Thrombelastograph as an adjunctive test in thrombophilia screening," Blood Coagulation and Fibrinolysis, vol. 15, No. 3, Apr. 2004, pp. 207-211.

O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.

Ophir, et al., "Elastography: A Quantitative Method for Imaging the Elasticity of Biological Tissues," Ultrasonic Imaging, vol. 13, No. 2, 1991, pp. 111-134.

Packham, M., "Role of platelets in thrombosis and hemostasis," Canadian Journal of Physiology and Pharmacology, vol. 72, No. 3, Mar. 1994, pp. 278-284.

Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.

Parsons, et al., "Age Determiniation of Experimental Venous Thrombi by Ultrasonic Tissue Characterization," Journal of Vascular Surgery, vol. 17, 1993, 470-478.

Patil, et al., "3D prostate elastography: algorithm, simulations and experiments," Physics in Medicine & Biology, vol. 52, No. 12, 2007, pp. 3643-3663.

Perry, et al., "Point-of-care testing in haemostasis," British Journal of Haematology, vol. 150, No. 5, Sep. 2010, pp. 501-514.

Pivalizza, et al., "Perioperative thromboelastography and sonoclot analysis in morbidly obese patients," Canadian Journal of Anaesthesia, vol. 44, No. 9, Sep. 1997, pp. 942-945.

Rao, G., "Need for a point-of-care assay for monitoring antiplatelet and antithrombotic therapies," Stroke, vol. 40, No. 6, Jun. 2009, pp. 2271-2272.

Riou, Chonavel et al., "Fast adaptive eigenvalue decomposition: a maximum likelihood approach," Signal Processing, 83, 2003, pp. 307-324.

Rubin, et al., "Clinical application of sonographic elasticity imaging for aging of deep venous thrombosis: preliminary findings," Journal of Ultrasound in Medicine, vol. 22, 2003, pp. 443-448.

Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.

Sarvazyan, et al., "Shear Wave Elasticity Imagining—A New Ultrasonic Technology of Medical Diagnostics," Ultrasound in Medicine and Biology, vol. 24, 1998, pp. 1419-1436.

Schmitt, C., et al., "Characterization of blood clot viscoelasticity by dynamic ultrasound elastography and modeling of the rheological behavior," Journal of Biomechanics, vol. 44, No. 4, 2011, pp. 622-629.

Shi, Quantitative Investigation of Acoustic Streaming in Blood, J. Acoust. Soc. Am. 111, Feb. 2002, pp. 1110-1121.

Shi, et al., "Color Doppler Detection of Acoustic Streaming in a Hematoma Model," Ultrasound in Medicine and Biology, vol. 27, No. 9, 2001, pp. 1255-1264.

Shi, et al., "Color Doppler imaging of acoustic streaming in blood and clot," IEEE Ultrasonics Symposium, vol. 2, 1999, pp. 1315-1318.

Shi, et al., "Experimental Investigation and Finite Element Simulation of Streaming in Blood in Cylindrical Models," IEEE Ultrasonics Symposium, vol. 2, 2000, pp. 1509-1512.

Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.

Shung, et al., "Ultrasonic characterization of blood during coagulation," Journal of Clinical Ultrasound, vol. 12, No. 3, 1984, pp. 147-153.

Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.

Spiel, A. O. et al.,"Validation of rotation thrombelastography in a model of systemic activation of fibrinolysis and coagulation in humans", Journal of Thrombosis and Haemostasis, 2006; 4: 411-416.

(56) References Cited

OTHER PUBLICATIONS

Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993;71:9-15.
Vig, et al., "Thromboelastography: a reliable test?" Blood Coagulation and Fibrinolysis, vol. 12, No. 7, Oct. 2001, 555-561.
Viola, et al., "A Comparison between spline-based and phase-domain time-delay estimators," IEEE Transactions on Ultrasonics, Ferroelectrics, and Frequency Control, vol. 53, No. 3, 2006, pp. 515-517.
Viola, Francesco, et al., "A Novel Ultrasound-Based Method to Evaluate Hemostatic Function of Whole Blood," Clin Chim Acta, vol. 411, Nos. 1-2, 2010, pp. 106-113.
Viola, et al., "A comparison of the performance of time-delay estimators in medical ultrasound," IEEE Transactions on Ultrasonics Ferroelectrics & Frequency Control., vol. 50, 2003, pp. 392-401.
Viola, et al., "A Spline Based Algorithm for Continuous Time Delay Estimation Using Sampled Data," IEEE Transactions on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Viola, et al., "Ultrasound echo decorrelation due to acoustic radiation force," IEEE Ultrasonics Symposium Proceedings, vol. 2, 2002, pp. 1903-1906.
Voleišis, A., et al., "Ultrasonic method for the whole blood coagulation analysis," Ultrasonics, vol. 40, May 2002, pp. 101-107.

Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Whitten, et al., "Thromboelastography: past, present, and future," Anesthesiology, vol. 92, No. 5, May 2000, pp. 1223-1225.
Yu, et al., "Single-Ensemble-Based Eigen-Processing Methods For Color Flow Imaging," IEEE Transactions on Ultrasonics, Ferroelectrics, and Frequency Controls, vol. 55, No. 3, 2008, pp. 573-587.
Azar et al., "Abciximab in Primary Coronary Angioplasty for Acute Myocardial Infarction Improves Short- and Medium-Term Outcomes", J. Am. Coll. Cardiol., Dec. 1998.; 32(7):1996-2002. PubMed P.M.I.D.: 9857884.
Born, G.V., "Aggregation of Blood Platelets by Adenosine Diphosphate and its Reversal". Nature, Jun. 9, 1962; 194:927-9. PubMed P.M.I.D.: 13871375.
Callé et al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010.; 36(2):295-305. PubMed P.M.I.D.: 20045589.
Coiffic et al., "Inhibition of Platelet Aggregation by Abciximab but not by Aspirin can be Detected by a New Point-of-Care Test, the Hemostatus". Thromb. Res., Jul. 15, 1999, 95(2):83-91. PubMed P.M.I.D.: 10418797.
Communication pursuant to Rule 114(2) EPC issued in European Patent Application No. 12865280.7, dated Dec. 13, 2016, 5 pages.
Communication pursuant to Rule 94(3)) EPC issued in European Patent Application No. 12865280.7, dated Jul. 3, 2017, 3 pages.
Declaration of U.S. Pat. No. 9,272, 280, 67 pages.
Declaration of U.S. Pat. No. 9,410,971, 124 pages.
Delhaye et al., Temperature corrected thromboelastometry in hypothermic trauma patients: 6AP24. European Journal of Anaesthesiology, May/Jun. 2008, 25:84.
Dorn-Beineke et al., "Evaluation of the Automated Coagulation Analyzer Sysmex CA-7000". Thromb. Res., 2005; 116(2):171 -9. PubMed P.M.I.D.:15907533.
Douning et al., "Temperature Corrected Thrombelastography in Hypothermic Patients". Anesthesia & Analgesia, Oct. 1995.; 81 (3):608-11.
Eikelboom et al., "Monitoring Unfractionated Heparin with the aPTT: Time for a Fresh Look". Thromb. Haemost. Nov. 2006.; 96(5):547-52. Review. PubMed P.M.I.D.: 17080209.
Extended European Search Report issued in European Patent Application No. 11766842.6, dated Oct. 21, 2015, 10 pages.
Extended Search Report issued in European Patent Application No. 12865280, dated Oct. 24, 2016, 5 pages.
Flanders et al., "Evaluation and Performance Characteristics of the STA-R Coagulation Analyzer". Clin Chem., Sep. 2002.; 48(9):1622-4. PubMed P.M.I.D.: 12194955.

(56) References Cited

OTHER PUBLICATIONS

Ganter et al., "Coagulation Monitoring: Current Techniques and Clinical Use of Viscoelastic Point-of-Care Coagulation Devices". Anesth. Analg., May 2008; 106(5):1366-75. Review. PubMed P.M.I.D.: 18420846.
Ganter et al., "Kaolin-Based Activated Coagulation Time Measured by Sonoclot in Patients Undergoing Cardiopulmonary Bypass." J. Cardiothorac. Vasc. Anesth, Aug. 2007.; 21(4):524-8. PubMed P.M.I.D.: 17678778.
Gorlinger et al., "Recommendations for using the ROTEM® in the management of perioperative bleeding in Cardiac Surgery" Recommendations from the ROTEM® Expert Meeting Working Group, Munich 2007, 10 pages.
Gosselin et al., "Monitoring Oral Anticoagulant Therapy with Point-of-Care Devices: Correlations and Caveats". Clin. Chem., Sep. 1997.; 43(9):1785-6. PubMed P.M.I.D.: 9299978.
Harrison, P. Platelet Function Analysis. Blood Rev. Mar. 2005.; 19(2):111-23. Review. PubMed P.M.I.D.: 15603914.
Hett et al., "Sonoclot Analysis". Br. J. Anaesth., Dec. 1995.; 75(6):771-6. Review. PubMed P.M.I.D.: 8672329.
Hirsh et al., "Oral anticoagulants. Mechanism of Action, Clinical Effectiveness, and Optimal Therapeutic Range". Chest. Oct. 1992.; 102(4 Suppl.):312S-326S. Review. PubMed P.M.I.D.: 1345417.
Ivandic et al.,"Determination of Clopidogrel Resistance by Whole Blood Platelet Aggregometry and Inhibitors of the P2Y12 Receptor". Clin. Chem., Mar. 2006.; 52(3):383-8. PubMed P.M.I.D.: 16423907.
Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995.; 110(1):36-45. PubMed P.M.I.D.: 7609566.
Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention". Am. J. Cardiol., Aug. 1999. 15; 84(4):391-5. PubMed P.M.I.D.: 10468074.
Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001.; 33(3):153-8. PubMed P.M.I.D.: 11680728.
Lang et al., "Multi-center investigation on reference ranges from ROTEM thromboelasatometry", Blood coagul. Fibrinol 16:4, 2005, pp. 301-310.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Li et al., "The Xylum Clot Signature Analyzer: A Dynamic Flow System that Simulates Vascular Injury". Thromb. Res., Dec. 15, 1998; 92(6 Suppl.2): S67-77. PubMed P.M.I.D.: 9886913.
Machado et al., "Evaluation of an Ultrasonic Method Applied to the Measurement of Blood Coagulation Time". Physiol. Meas., May 1997; 18(2):129-43. PubMed P.M.I.D.: 9183807.
Motovska et al., "Benefits and Risks of Clopidogrel Use in Patients with Coronary Artery Disease: Evidence from Randomized Studies and Registries". Clin. Ther., 2008; 30 Pt. 2:2191-202. J. Clinthera., 2008.12.001. Review. PubMed P.M.I.D.: 19281914.
Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009.; 15(6):652-9. PubMed P.M.I.D.: 18805846.
Nam et al., "Evaluation of the Roche CoaguChek XS Handheld Coagulation Analyzer in a Cardiac Outpatient Clinic". Ann. Clin. Lab. Sci., 2008 Winter; 38(1):37-40. PubMed P.M.I.D.: 18316780.
Pallister CJ, Watson MS (2010). Haematology. Scion Publishing, pp. 336-347. ISBN 1-904842-39-9.
Patent Examination Report issued in Australian Application No. 2012364908, dated Jul. 23, 2016, 4 pages.

Peeters et al., "Ultrasonic Measurements of Coagulation and Fibrinolysis". J. Clin. Pathol., May 1964; 17:320-3. PubMed P.M.I.D.: 14159472; PubMed Central P.M.C.I.D.: PMC480759.
Petition For Inter Partes Review of U.S. Pat. No. 9,272,280 B2, 28 Pages.
Petition For Inter Partes Review of U.S. Pat. No. 9,410,971 B2, 51 Pages.
Petition For Inter Partes Review of U.S. Pat. No. 9,410,971, dated Nov. 30, 2017, 74 pages.
Decision Denying Petitioner's Request for Rehearing for Inter Partes Review of U.S. Pat. No. 9,410,971, entered Nov. 3, 2017, 7 pages.
Patent Owner's Response to the Decision to Institute Inter Partes Review of U.S. Pat. No. 9,410,971, entered Dec. 1, 2017, 59 pages.
Declaration of Dr. Scott Diamond, Ph.D., dated Dec. 1, 2017.
Price et al., "Prognostic Significance of Post-Clopidogrel Platelet Reactivity Assessed by a Point-ofCcare Assay on Thrombotic Events after Drug-Eluting Stent Implantation". Eur. Heart J., Apr. 2008.; 29(8):992-1000. PubMed P.M.I.D.: 18263931.
Prisco et al. "Point-of-Care Testing of Hemostasis in Cardiac Surgery". Thromb. J. May 6, 2003; 1(1):1, 10 pages. PubMed P.M.I.D.: 12904262; PubMed Central P.M.I.D.: PMC166118.
Rugeri et al., "Diagnosis of early coagulation abnormalities in trauma patients by rotation thrombelastography", Journal of Thrombosis and Haemostasis, 5, 2007, pp. 289-295.
Rumbaut et al. "Platelet-Vessel Wall Interactions in Hemostasis and Thrombosis" (2010), San Rafael (CA): Morgan & Claypool Life Sciences, 5 pages.
Ruzicka, K., et al. Evaluation of Bedside Prothrombin Time and Activated Partial Thromboplastin Time Measurement by Coagulation Analyzer COAGUCHECK PLUS in Various Clinical Settings. Throm. Res., 87(5)1997 pp. 431-440. See also, Hillman, R., 1988 U.S. Pat. No. 4,756,884. Capillary Fill Device.
S. Kozek-Langenecker, Intensive Care Medicine, Annual Update 2007, Monitoring of Hemostasis in Emergency Medicine, pp. 847-860, Springer New York.
Scharbert et al., "Evaluation of the Platelet Mapping Assay on Rotational Thromboelastometry ROTEM". Platelets. Mar. 2009;20(2):125-30. PubMed P.M.I.D. 19235055.
Schochl et al., "Use of rotation thromboelastometry (ROTEM) to achieve successful treatment of polytrauma with fibrinogen concentrate and prothrombin complex concentrate", Anaesthesia, 2010, 65, pp. 199-203.
Taborski et al., "Analytical Performance of the New Coagulation Monitoring System INRatio for the Determination of INR Compared with the Coagulation Monitor Coaguchek S and an Established Laboratory Method" J. Thromb.Thrombolysis. Oct. 2004.; 18(2):103-7. PubMed P.M.I.D.: 15789176.
Third party observation filed in European Patent Application No. 11766842.6, dated Mar. 6, 2016, 10 pages.
Third party observation filed in U.S. Appl. No. 15/202,059, filed Nov. 30, 2016, 40 pages.
Tripodi et al., "International Sensitivity Index Calibration of the Near-Patient Testing Prothrombin Time Monitor, ProTime". Am. J. Clin. Pathol., Feb. 2003.;119(2):241-5. PubMed P.M.I.D.: 12579994.
Versteeg et al., "New Fundamentals in Hemostasis", Physiol. Rev. Jan. 2013.; 93(1):327-58. Review. PubMed P.M.I.D.: 23303912.
Viola et al., "A Novel Ultrasound-Based Method to Evaluate hemostatic Funtion of Whole Blood", Clin Chim Acta. Jan. 2010; 411(1-2): 106-113., Published online Oct. 25, 2009, PubMed Central P.M.C.I.D. PMC2791922.
Wolff et al., "Aspirin for the Primary Prevention of Cardiovascular Events: an Update of the Evidence for the U.S. Preventive Services Task Force". Ann. Intern. Med., Mar. 17, 2009; 150(6):405-10. Review. PubMed P.M.I.D.: 19293073.
Examination Report issued in Australian Application No. 2012364908, dated Jun. 27, 2017, 5 pages.
Trial Board Order For Inter Partes Review of U.S. Pat. No. 9,272,280 B2, 13 pages.
Trial Board Order For Inter Partes Review of U.S. Pat. No. 9,410,971 B2, 27 pages.
Office Action received in co-pending U.S. Appl. No. 15/202,059, dated Oct. 4, 2016.

(56) References Cited

OTHER PUBLICATIONS

Office Action received in co-pending U.S. Appl. No. 15/202,059, dated Jul. 13, 2017.
Advisory Action received in co-pending U.S. Appl. No. 15/202,059, dated Sep. 21, 2017.
Office Action received in co-pending U.S. Appl. No. 15/202,059, dated Jan. 12, 2018.
Notice of allowance received in co-pending U.S. Appl. No. 15/202,059, dated May 23, 2018.
Corrected Notice of allowance received in co-pending U.S. Appl. No. 15/202,059, dated Jun. 22, 2018.
Office Action received in co-pending U.S. Appl. No. 15/904,984, dated Jul. 12, 2018.
Patent Owner's Response to the Decision to Institute Inter Partes Review of U.S. Pat. No. 9,272,280, dated Dec. 1, 2017, 39 pages.
Declaration of Patrick D. Mize, Ph.D., dated Nov. 30, 2017.
Table of Prior Art Devices.
Gorlinger, K., et al., "Perioperative Coagulation Management and Control of Platelet Transfusion by Point-of-Care Platelet Function Analysis," Transfus Med Hemother 34:396-411 (2007).
Rahe-Meyer, N. et al., Multicentric comparison of single portion reagents and liquid reagents for thromboelastometry. Blood Coagul Fibrinolysis Apr. 2009;20(3):218-22. PubMed P.M.I.D.: 19657320.
Stony Brook Portable Field Viscometer (For a quick 'Pass' or 'Fail' decision).
Faulds, D. et al., "Abciximab (c7E3 Fab). A review of its pharmacology and therapeutic potential in ischaemic heart disease; Drugs 583-98 (1994)" PubMed P.M.I.D.: 7528131 ("Faulds 1994").
Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18. 1994.
Wolberg AS. Plasma and cellular contributions to fibrin network formation, structure and stability. Haemophilia. May 16, 2010:7-12.
Janus TJ, Lewis SD, Lorand L, Shafer JA. Promotion of thrombin-catalyzed activation of factor XIII by fibrinogen. Biochemistry. 1983;22(26):6269-72.
Niewiarowski S, Stewart GJ, Nath N, Sha AT, Lieberman GE. ADP, thrombin, and Bothrops atrox thrombinlike enzyme in platelet-dependent fibrin retraction. The American journal of physiology. 1975;229(3):737-45.
Janmey PA, Erdile L, Bale MD, Ferry JD. Kinetics of fibrin oligomer formation observed by electron microscopy. Biochemistry. 1983;22(18):4336-40.
Blättler W, Straub PW, Peyer A. Effect of in vivo produced fibrinogen-fibrin intermediates on viscosity of human blood. Thrombosis research. 1974;4(6):787-801.
Weisel JW. The mechanical properties of fibrin for basic scientists and clinicians. Biophysical Chemistry. 2004;112(2-3):267-276.

Cuisset T, Frere C, Poyet R, et al. Clopidogrel response: Head-to-head comparison of different platelet assays to identify clopidogrel non-responder patients after coronary stenting. Archives of Cardiovascular Diseases. 2010;103(1):39-45.
Multiplate® Analyzer Product Guide.
VerifyNow® Product Guide.
Kuntamukkula MS, McIntire L V, Moake JL, Peterson DM, Thompson WJ. Rheological studies of the contractile force within platelet-fibrin clots: effects of prostaglandin E1, dibutyryl-cAMP and dibutyryl-cGMP. Thrombosis research. 1978;13(6):957-69.
Plotkin, et al., The Journal of Trauma: Injury, Infection, and Critical Care. 2008.
Fundamentals of biomechanics Equiolobrium, Motion, and Deformation. 2nd Edition. Eds. Nihat Özkaya and Margareta Nordin. (Springer Science+Business Media, Inc., New York, NY). Chapter 9 "Mechanical Properties of Biological Tissues." pp. 196-218. 1999.
Fundamentals of biomechanics Equiolobrium, Motion, and Deformation. $3^{rd}$ Edition Eds. Nihat Özkaya and Margareta Nordin. (Springer Science+Business Media, Inc., New York, NY). Chapter 15 "Mechanical Properties of Biological Tissues". pp. 221-236. 2012.
Instrument Engineers' Handbook. Fourth Edition. Ed. Bela G. Liptak (CRC Press). Process Measurement and Analysis vol. 1, Chapter 8 Analytical Instrumentation. 8.53 Rheometers, 1628-1636, 2003.
Thurston GB. Viscoelasticity of Human Blood. Biophysical Journal. 1972; 12:1205-1217.
Webster, Medical Instrumentation: Application and Design, New York: John Wiley & Sons, 1998, 6 pages.
Patent Owner's Preliminary Response to Petition Requesting Inter Partes Review of U.S. Pat. No. 9,410,971, dated Feb. 14, 2018, 33 pages.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Lang et al., "Possibilities and limitations of thromboelastometry/thromboelastography," Downloaded from www.haemostaseologie-online.com on Mar. 6, 2018 | IP: 24.163.60.123.
Communication pursuant to Article 94(3) EPC dated Apr. 3, 2018 in co-pending European Application No. 12865280.
Office Action issued for Canadian Application No. 2,823,729, dated Mar. 9, 2018.
Examination Report issued for Australian Application No. 2017248548, dated Jul. 9, 2018.
International Search Report and Written Opinion for International Application No. PCT/US2018/028630 dated Oct. 31, 2018.
First Office Action issued in corresponding Chinese Appiication No. 2018800356900, dated Feb. 2, 2021.

\* cited by examiner

DISPOSABLE SYSTEM FOR ANALYSIS OF HEMOSTATIC FUNCTION

RELATED APPLICATIONS

This application claims priority to, and the benefit of, U.S. Provisional Appl. No. 62/488,045, filed Apr. 20, 2017, titled "Disposable System for Analysis of Hemostatic Function," which is incorporated by reference herein in its entirety.

GOVERNMENT LICENSE RIGHTS

The invention was made with government support under grant R44HL103030 awarded by National Heart Lung and Blood Institute. The government has certain rights in the invention.

TECHNICAL FIELD

The present application relates to devices, systems and methods for evaluating hemostasis in a subject by preparation and analysis of a test sample from the subject.

BACKGROUND

Hemostasis, the physiological control of bleeding, is a complex process incorporating the vasculature, platelets, coagulation factors, fibrinolytic proteins, and a variety of activators and inhibitors. Disruption of hemostasis plays a central role in the onset of myocardial infarction, stroke, pulmonary embolism, deep vein thrombosis and excessive bleeding. Consequently, in vitro diagnostics (IVD) are critically needed to quantify hemostatic function/dysfunction and direct appropriate treatment.

The process of coagulation is highly dependent, among other things, on the temperature at which it takes place. Under normal conditions, coagulation occurs at body temperature, which is optimal for the proper enzymatic action of the clotting factors in the cascade.

Preparation of the blood to be tested is also important, as the manner a blood sample is prepared prior to its evaluation can affect, for example, the actions of the vasculature components, platelets and other cellular components, coagulation factors, fibrinolytic components, and any inhibitor or activator of hemostasis.

SUMMARY

Provided are devices, systems and methods for evaluation of hemostasis. For example, provided are disposable systems for analysis of hemostasis function. The disposable system, in some embodiments, includes a multi-channel or multi-chamber test cartridge device configured to operate with a testing system for evaluation of hemostasis in a subject by in vitro evaluation of a test sample from the subject. The disposable system, in some embodiments, is configured to interrogate the test sample to evaluate clot stiffness, strength, or other mechanical properties of the test sample to assess the function of various physiological processes occur during coagulation and/or dissolution of the resulting clot. The sample can include in whole, or in part, whole blood, plasma, platelet rich plasma, or platelet poor plasma. Furthermore, the sample can include one or more reagent (such as anticoagulants or anti-platelet drugs that might be present in the blood as collected), or one or more pharmacological treatment (such as in the case of heparin or low molecular weight heparin) or other inert components (such as polystyrene beads) that are added to the test sample before the cartridge device being used. The disposable system facilitates the point of care evaluation of hemostasis of a test sample that is robust (e.g., can be performed in non-laboratory environment), rapid (e.g., only to take a few minutes to perform), easy-to-use and provides clear results (e.g., that are direct to the functional components of hemostasis), and facilitates identification of exact hemostasis defects. The exemplified device automates one or more pre-measurement steps that minimizes sample manipulation steps required for the user, thereby improving test reproducibility and/or test quality. The disposable system, in some embodiments, includes a plurality of testing circuits each having a pathway defined by channels and chambers configured to prepare a test sample of blood for evaluation by a measurement device. In each testing circuit, a portion of the test sample is introduced to a reagent or combination of reagents specific to that testing circuit.

The disposable system, in some embodiments, is configured to condition the respective test samples prior to, during, and/or after the mixing with the reagent(s), to optimize the proper actions of applicable blood component and chemistry (e.g., vasculature components, platelets or other cellular components, coagulation factors, fibrinolytic components, and any other inhibitor or activator of hemostatic function, etc.) being evaluated.

In an aspect, an apparatus (e.g., a cartridge) is disclosed for the assessment of hemostasis. The apparatus includes a housing; an input port integrally formed with the housing that is structurally configured to establish fluidic communication and evacuate contents of a sample holding tube; and a first chamber in fluidic communication with the input port, the first chamber being configured to receive a sample contained in the sample holding tube and to condition the received sample to a desired temperature (e.g., a pre-defined temperature range) before the received sample is allowed to contact one or more reagents located in one or more fluidic circuits downstream to the first chamber, wherein each of the one or more fluidic circuits comprises i) a second chamber in fluidic communication with the first chamber that meters the sample in the first chamber into an aliquot, wherein the metered sample is introduced to a reagent, or a combination of reagents, (e.g., in the form of lyophilized reagent bead) located in a corresponding fluidic circuit (e.g., a reagent pocket) to form a mixed sample and ii) a testing chamber in fluidic communication with the second chamber, the testing chamber being structurally configured for interrogation by a measurement system configured to determine properties (e.g., mechanical properties or viscoelastic properties) of the mixed sample.

In some embodiments, at least one of the one or more fluidic circuits comprise one or more pockets (e.g., each configured to house a lyophilized reagent bead comprising a reagent, or a combination of reagents).

In some embodiments, at least one of the one or more fluidic circuits comprise one or more liquid-retaining pockets (e.g., each configured to house an assay, in liquid form, comprising the reagent, or a combination of reagents).

In some embodiments, at least one of the one or more fluidic circuits includes one or more lyophilized reagents that are located on one or more surfaces thereof (e.g., lyophilized on each of the surfaces; lyophilized as films placed on, or adhered to, one or more of the surfaces).

In some embodiments, at least one of the one or more fluidic circuits includes one or more reagents that are processed onto surfaces thereof (e.g., dried on the surfaces; spray coated on the surfaces; baked onto the surfaces).

In some embodiments, the input port is communicatively coupled to a pressure port, wherein pressure applied to the pressure port causes the evacuation of the contents of the sample holding tube through the input port to first chamber.

In some embodiments, the input port comprises a needle assembly.

In some embodiments, the needle assembly comprises the input port and a second port, wherein the second port is configured to vent a liquid or gas into the sample holding tube so as to promote evacuation of the contents therein. The input port, in some embodiments, is located (e.g., concentrically located) within a second port configured to vent a liquid or gas into the sample holding tube so as to cause evacuation of the contents of the sample holding tube.

In some embodiments, the input port comprises a luer lock configured to connect to the sample holding tube, wherein the sample holding tube is a syringe.

In some embodiments, the input port is communicatively coupled to a first pressure port, wherein pressure when applied to the first pressure port causes the evacuation of the contents of the sample holding tube through the input port to the first chamber.

In some embodiments, the first chamber is configured to mate with a corresponding thermal regulating system (e.g., heating/cooling system) of the measurement system to condition the received sample to, or near, the desired temperature.

In some embodiments, the shape and/or materials of the first chamber are optimized to facilitate thermal regulation (e.g., heating and/or cooling) of the sample to, or near, the desired temperature.

In some embodiments, the first chamber is configured to mate with a corresponding thermal regulating surface of a sub-system component of the measurement system to condition the received sample to, or near, the desired temperature. In some embodiments, a channel portion of the one or more fluidic circuits is configured to mate with a corresponding heating/cooling system of the measurement system to condition the received sample to, or near, the desired temperature.

In some embodiments, a channel portion of the one or more fluidic circuits is configured to mate with a corresponding thermal regulating system of the measurement system to condition the received sample to the desired temperature. In some embodiments, the first chamber and/or the channel portion of the one or more fluidic circuits is in physical proximity (e.g., physical contact or near contact) with a sensor configured to measure a temperature of the sample received in the first chamber.

In some embodiments, the sensor is selected from group consisting of a thermistor, a thermocouple, and an optical sensor (e.g., an IR sensor).

In some embodiments, the apparatus includes a first pressure port in fluidic communication with the first chamber, the first pressure port being configured to receive negative or differential pressure (e.g., for filling the first chamber); and a filter positioned within the first pressure port in at least one of the fluidic circuits (e.g., such that the filter is clogged by the sample received in the first chamber when the first chamber is full). The filter, in some embodiments, is configured to allow air to move through the first pressure port but prevent fluid from moving there through.

In some embodiments, the apparatus includes a first pressure port configured to receive negative or differential pressure for filling the first chamber; and a first fluidic pathway extending from the first pressure port to the first chamber, wherein the filter is positioned within the first pressure port.

In some embodiments, for each of the one or more fluidic circuits, the fluidic communication between the first chamber and the second chamber is through a second fluid pathway originating from a side of the first chamber (e.g., a side wall, a bottom wall, and etc.) (e.g., such that bubbles present in the received sample are trapped away from the second chamber).

In some embodiments, each of the one or more fluidic circuits comprises a third fluid pathway in fluidic communication with the second chamber, wherein the third fluidic pathway leads a second pressure port configured receive negative or differential pressure for filling the second chamber.

In some embodiments, the second pressure port has a second filter therein, wherein the second filter is configured to clog when the second chamber is filled.

In some embodiments, the apparatus includes one or more fluidic pathways in fluidic communication with the second pressure port for all of the one or more fluidic circuits, wherein the one or more fluidic pathways are configured to provide the negative pressure to the second pressure port for all of the one or more fluidic circuits.

In some embodiments, for each of the one or more fluidic circuits, the second chamber is in fluidic communication with a vent port, wherein the vent port is configured to be closed while the sample is metered into the aliquot in the second chamber and further configured to be open to atmospheric pressure after the sample is metered into the aliquot in the second chamber.

In some embodiments, each of the one or more fluidic circuits comprises a third set of fluid pathways in fluidic communication between a respective second chamber (e.g., metering chamber) and test chamber, wherein a portion of third set of fluid pathways are arranged as a serpentine-shaped conduit or channel.

In some embodiments, each of the one or more fluidic circuits further comprises a serpentine reservoir between the testing chamber and the second chamber.

In some embodiments, the metered sample is alternatively directed through portions of the one or more fluidic circuits to facilitate mixing of the metered sample and the reagent, or a combination of reagents.

In some embodiments, the metered sample is alternatively and multiplicatively directed, for each of the one or more fluidic circuits, between a first position (e.g., the second chamber) in a fluidic circuit a second position (e.g., a position in the serpentine reservoir) in the fluidic circuit.

In some embodiments, each of the one or more fluidic circuits further comprises a third pressure port in fluidic communication with the second chamber and the testing chamber, the third pressure port configured to receive negative or differential pressure (e.g., for drawing the aliquot from the second chamber to the testing chamber), wherein the third pressure port is further configured to alternately receive alternating pressure, e.g., for alternately drawing the aliquot from the second chamber along the serpentine reservoir and pushing the aliquot through the serpentine reservoir to the second chamber.

In some embodiments, the serpentine reservoir includes an optical detection zone to facilitate optical detection of the metered sample in the serpentine reservoir or a location of the sample in the serpentine reservoir.

In some embodiments, each of the one or more fluidic circuits further comprises a mixing pathway between the testing chamber and the second chamber, the mixing pathway comprising one or more ferromagnetic beads or bars therein.

In some embodiments, at least one of the one or more fluidic circuits comprises one or more quality testing portals.

In some embodiments, the one or more quality testing portals is configured to be sensed optically, wherein the quality testing port is transparent.

In some embodiments, the one or more quality testing portals is configured to be sensed electrically, wherein quality testing port comprises one or more sensing electrodes.

In some embodiments, the one or more quality testing ports is configured to be sampled for characteristics for the metered sample (e.g., for pressure, presence of flow, flow rate, temperature).

In some embodiments, for each of the one or more fluidic circuits, the testing chamber comprises a mechanism to couple energy into the testing chamber to perform the measurements such as in the case of a lens configured to direct ultrasonic pulses into to the testing chamber.

In another aspect, an apparatus is disclosed for the assessment of hemostasis, the apparatus comprising: a housing; an input port integrally formed with the housing that is structurally capable of establishing fluidic communication with, and evacuating contents of, a sample holding tube; a first chamber that is in fluidic communication with the input port that receives the sample contained in the evacuated tube and whereby the sample temperature is adjusted to a desired temperature before the sample contacting one or more reagents; one or more second chambers that are in fluidic communication with the first chamber, the one or more second chamber being configured to meter the sample in the first chamber into one or more aliquots; one or more reagent pockets each filled with one or more lyophilized reagent bead that are in fluidic communication with each of the aliquot chambers and permits the sample present in each aliquot to be mixed with said one or more reagent beads; and one or more testing chambers that are in fluidic communications with the aliquot chambers and that are structurally capable of being interrogated to determine the sample viscoelastic properties after such sample has been mixed with the one or more reagents.

In some embodiments, the reagent, or combination of reagents, located in the one or more fluidic circuits includes an intrinsic pathway activator (e.g., kaolin, celite, glass, ellagic acid, micronized silica, Hageman factor, etc.) or a combination therewith.

In some embodiments, the reagent, or combination of reagents, located in the one or more fluidic circuits includes an extrinsic pathway activator (e.g., tissue factor, recombinant tissue factor, thromboplastin, etc.) or a combination therewith.

In some embodiments, the reagent, or combination of reagents, located in the one or more fluidic circuits includes a coagulation activator (e.g., thrombin, factor Xa, reptilase, ecarin, Russell's viper venom or other snake venoms, etc.) or a combination therewith.

In some embodiments, the reagent, or combination of reagents, located in the one or more fluidic circuits includes a platelet activator or platelet inhibitor (e.g., GPIIb/IIIa inhibitors (e.g., abciximab, eptifibatide, tirofiban, roxifiban, orbofiban), cytochalasin D, blebbistatin, PAR1 inhibitors, PAR4 inhibitors, glycoprotein IB inhibitors, TRAP, ADP, arachidonic acid, ADP inhibitors, non-steroidal anti-inflammatory drugs, platelet activating factor, ristocetin, epinephrine, etc.) or a combination therewith.

In some embodiments, the reagent, or combination of reagents, located in the one or more fluidic circuits includes a fibrinolytic functions activator or inhibitor (e.g., tPA, uKA, streptokinase, TAFIa, plasmin/plasminogen, aprotinin, epsilon-aminocaproic acid, tranexamic acid, plasminogen activator inhibitor 1 (PAI1), $\alpha$2-antiplasmin ($\alpha$2-AP), or plasmin-antiplasmin complexes, carboxypeptidase inhibitor) or a combination therewith.

In some embodiments, the reagent, or combination of reagents, located in the one or more fluidic circuits includes FXIIIa inhibitors or a combination therewith.

In some embodiments, the reagent, or combination of reagents, located in the one or more fluidic circuit includes thrombomodulin or a combination therewith.

In some embodiments, the reagent, or combination of reagents, located in the one or more fluidic circuit includes low molecular weight heparin or a combination therewith.

In some embodiments, the reagent, or combination of reagents, located in the one or more fluidic circuits includes Hexadimethrine bromide (polybrene) or a combination therewith.

In some embodiments, the reagent, or combination of reagents, located in the one or more fluidic circuits includes heparin or a combination therewith.

In some embodiments, the reagent, or combination of reagents, located in the one or more fluidic circuits includes corn trypsin inhibitor or a combination therewith.

In some embodiments, the reagent, or combination of reagents, located in the one or more fluidic circuits includes adenosine or a combination therewith.

In some embodiments, the reagent, or combination of reagents, located in the one or more fluidic circuits includes GPRP (Gly-Pro-Arg-Pro) or a combination therewith.

In some embodiments, the reagent, or combination of reagents, located in the one or more fluidic circuits includes calcium or a combination therewith.

In some embodiments, the reagent, or combination of reagents, located in the one or more fluidic circuits includes fibronectin or a combination therewith.

In some embodiments, the reagent, or combination of reagents, located in the one or more fluidic circuits includes collagen or a combination therewith.

In some embodiments, the reagent, or combination of reagents, located in the one or more fluidic circuits includes an immuno-detection reagent or a combination therewith.

In some embodiments, the reagent, or combination of reagents, located in the one or more fluidic circuits includes heparinase I or a combination therewith.

In some embodiments, the reagent, or combination of reagents, located in the one or more fluidic circuits includes endothelial cells or activated endothelial cells.

In some embodiments, the measurement system is selected from the group consisting of a sonorheometry-based system, thromboelastography-based system, a thromboelastometry-based system, an optical-based system, a fluorescence-based system, a colorimetric-based system, an aggregometry-based system, a resonance-based system, and an electrical impedance-based system.

In another aspect, a method is disclosed of mixing a sample with one or more reagents in an apparatus (e.g., a cartridge) and testing the mixed sample for the assessment of hemostasis. The method includes receiving a plurality of metered samples of from a plurality of metering chambers that received test fluid from a sample holding tube (e.g., via a mechanical coupling that connects the apparatus to the sample holding tube or via an opening to which sample from the sample holding tube is placed); alternately and multiplicatively flowing each of the aliquots until the aliquot is mixed with a reagent, or a combination of reagents, to form a mixed aliquot, wherein the at least one aliquot alternately and cyclically flowed i) in a first direction from the metering chamber through one or more reagent pocket, with the one or more reagents therein (e.g., lyophilized reagent bead), and along a serpentine pathway in communication with the metering chamber until at least a portion of the aliquot reaches a detection zone located in, or after, the serpentine pathway and ii) in a second direction from the detection zone reversed to the first direction through at least a portion of the serpentine pathway toward the metering chamber until a trigger event; and driving the mixed aliquot in a testing chamber in fluidic communication with the metering chamber, wherein the testing chamber is structurally configured for interrogation by a measurement system configured to determine properties (e.g., mechanical properties or viscoelastic properties) of the mixed aliquot, and wherein an interrogation of the testing chamber is performed with the mixed aliquot located therein.

In some embodiments, the method includes receiving the fluid in a first chamber configured to substantially adjust the temperature of the test sample toward body temperature or other desired temperatures, wherein the metered sample received in the metering chamber is received from the first chamber.

In some embodiments, the test fluid is moved into the first chamber in response to an applied pressure that is applied by, or generated from, the measurement system.

In some embodiments, the method includes conditioning the test fluid in the first chamber to, or substantially near, a desired temperature, wherein the test fluid is mixed with the one or more reagents following exit from the first chamber.

In some embodiments, the method includes isolating (e.g., blocking via a valve) the test fluid in the metering chamber to prevent the test fluid from contacting the one or more reagents during the filling of the metering chamber.

In some embodiments, a second applied positive or negative pressure is applied by, or generated from, the measurement system (e.g., applied at a second pressure port in communication with the) at a second port in communication with the serpentine pathway so as to move the at least one aliquot in the second direction.

In some embodiments, the first applied positive or negative pressure is applied by, or generated from, the measurement system in reversed so as to move the at least one aliquot in the second direction.

In some embodiments, the operation of receiving the mixed aliquot in the testing chamber further comprises receiving a negative pressure via the third pressure port, wherein the third pressure port is further in fluid communication with the testing chamber.

In some embodiments, the testing chamber is downstream of the serpentine pathway and the third pressure port is downstream of the testing chamber.

These and other features and advantages of the present invention will become more readily apparent to those skilled in the art upon consideration of the following detailed description and accompanying drawings, which describe both the preferred and alternative embodiments of the present invention.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 5B further shows the cartridge body of FIG. 5A further coupled to a sample holding tube, in accordance with an illustrative embodiment.

DETAILED DESCRIPTION

Figure 1:
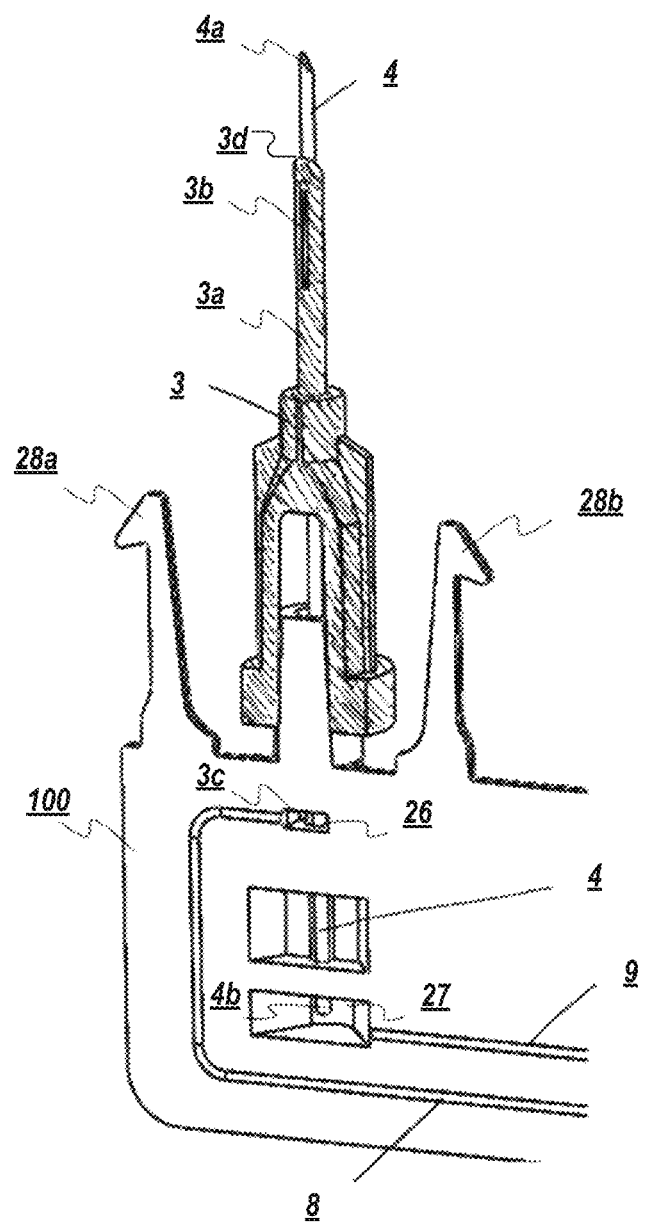
FIG. 1 shows a perspective view of an example biological sample input of a cartridge for use in a disposable system, in accordance with an illustrative embodiment.

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

As used throughout, by a "subject" is meant an individual. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex.

The apparatus described here includes a single-use cartridge apparatus configured to facilitate in vitro assessment of one or more hemostatic functions. Hemostatic function refers to a functional role of various blood components such coagulation factors, fibrinogen, platelets, fibrinolytic factors, and components of the vasculature. The cartridge apparatus and associated measurement system, in some embodiments, are configured to assess hemostatic function by measuring changes in at least one mechanical property of the tested sample when such sample is exposed to one or more reagents. In some embodiments, the cartridge apparatus and its test chambers are configured to facilitate measurements of viscoelastic properties, e.g., based on interrogation using ultrasound pulses or ultrasonic energy. However, other interrogation systems may be used with a cartridge apparatus with the features described herein. Examples of other interrogation systems includes, for example, but not limited to, systems that employ cup/pin technologies (such as in the case of thromboelastography and thromboelastometry), oscillating piston to measure changes in mechanical impedance, optical sensing, fluorescence sensing, colorimetric sensing, aggregometry, resonance sensing, or electrical impedance sensing, among others.

A broad array of reagents can be utilized in the cartridge apparatus, including intrinsic pathway activators (without limitations kaolin, Hageman factor, celite, glass, ellagic acid, micronized silica etc), extrinsic pathway activators (without limitations tissue factor, recombinant tissue factor, thromboplastin, etc), other coagulation activators (without limitations thrombin, factor Xa, reptilase, ecarin, Russell's viper venom or other snake venoms, etc), platelet activators or platelet inhibitors (without limitations GPIIb/IIIa inhibitors (such as abciximab, eptifibatide, tirofiban, roxifiban, orbofiban), cytochalasin D, blebbistatin, PAR1 inhibitors, PAR4 inhibitors, glycoprotein D3 inhibitors, TRAP, ADP, arachidonic acid, ADP inhibitors, non-steroidal anti-inflammatory drugs, etc.), fibrinolytic function activators or fibrinolytic function inhibitors (without limitations tPA, uKA, streptokinase, TAFIa, plasmin/plasminogen, aprotinin, epsilon-aminocaproic acid, tranexamic acid, plasminogen activator inhibitor 1 (PAI1), $\alpha$2-antiplasmin ($\alpha$2-AP), or plasmin-antiplasmin complexes, carboxypeptidase inhibitor, etc.), and others (FXIIIa inhibitors, Hexadimethrine bromide (polybrene), heparinase (e.g., heparinase I), ristocetin, heparin, low molecular weight heparin, corn trypsin inhibitor, adenosine, GPRP, calcium, fibronectin, collagen, epinephrine, immuno-detection reagents, direct thrombin inhibitors, factor Xa inhibitors, reagents aimed at reversing or eliminating the effects of the new oral anticoagulants (such as the direct thrombin inhibitors and the factor Xa inhibitors), thrombomodulin, etc.). Additional non-functional reagents could also be used to preserve the functionality of the other reagents (buffers and stabilizers for lyophilization or drying, dyes, etc.).

Reagents, in some embodiments, are placed and stored in chambers (e.g., pockets located within a fluidic circuit) in the cartridge apparatus but in alternative embodiments reagents can be placed and stored in various chambers or fluidic channels in the fluidic circuit of the cartridge apparatus. A fluidic circuit generally refers to one or more fluidic pathways established between sample preparation and the one or more test chambers where samples are ultimately measured.

In some embodiments, reagents are placed and stored in the cartridge apparatus in liquid forms or can be lyophilized in spheres (such as in the case of the Lyopheres™ produced by BioLyph LLC), lyophilized in films, lyophilized on the plastic surfaces, dried on the plastic surfaces, or spray coated, etc., in order to improve shelf-life stability. A person of ordinary skills in the art should recognize that these reagents are not fully inclusive and other reagents or reagent combinations that are inhibitors or activators of one or more hemostatic functions could be used in this cartridge.

The cartridge apparatus disclosed here is a component of a measurement system (e.g., a hemostasis measurement system). The measurement system (also referred to as the instrument) includes at least an interface element which couples between the cartridge apparatus and a measuring element configured to measures viscoelastic properties or mechanical properties of a sample processed within the cartridge apparatus. The measured viscoelastic properties or mechanical properties are outputted as results to a user interface. An example user interface is described in commonly assigned U.S. Pub. No. 2011/0252352 to Viola et al., which is incorporated by reference herein in its entirety.

In some embodiments, the interface element includes one or more heating and/or cooling elements.

In some embodiments, the interface element includes a fluidic manifold that facilitate connection to one or more pump elements and one or more valves.

In some embodiments, the interface element includes one or more sensors, e.g., configured to perform hemostasis measurements. The one or more sensors, in some embodiments, includes ultrasound sensors. In other embodiments, the one or more sensors includes other interrogative devices that is based on thromboelastography, thromboelastometry (e.g., a thromboelastography-based system or a thromboelastometry-based system), or that measures changes in mechanical impedance, changes in perturbation as observed via an optical-based system (e.g., having an optical sensor), fluorescence, colorimetric-based system, aggregometry-based system (e.g., having optical sensor, acoustic sensor, or electrodes that measure aggregation with the test sample), resonance-based system (e.g., having optical, acoustic, or mechanical position sensors that measures the sample when the sample is at, or near resonance), electrical impedance-based system (e.g., having electrodes configured to measure electrical impedance), or a combination thereof.

In some embodiments, the interface element includes a mechanical clamp configured to position the cartridge apparatus in a desired orientation with respect to the components (the one or more sensors, the fluidic manifold, the heating and/or cooling elements, and etc.) of the measurement system. When the interface element is interfaced with the components of the measurement system, the cartridge apparatus, in some embodiments, is driven via a series of controlled actions orchestrated by the measurement system to prepare the test sample for measurement. In some embodiments, the preparation operations include sample aspiration of a sample from a sample container (also referred to as a sample holding tube), sample heating and/or cooling, sample metering, sample mixing with reagents, and sample measurement. Each step, with reference to various embodiments, is described below. After measurements are completed, the results are output in the instrument user interface. In some embodiments, the cartridge apparatus and its internal components are the only component that directly contact with a sample to be analyzed.

In some embodiments, the cartridge includes computer readable information that can be optically or communicatively interrogated (e.g., RFID tags, computer readable medium such as flash ICs, QR codes, BAR codes, and etc.) and/or human readable information (e.g., labels).

The various embodiments described below does not utilize any active valve element in the cartridge design, but instead relies on a fluidic manifold and one or more valves placed in the instrument. Fluid is moved through the various cartridge components via pressure differential and/or gravity and/or material properties (such as in the case of hydrophobicity or hydrophilicity) and/or capillary forces.

In these embodiments, the cartridge is configured to couple with the instrument via one or more connection ports that are aligned via alignment slots. The connection ports include one or more pressure ports and one or more vent ports. However, in alternative embodiments, actuated valves (such as in the case of elastomeric valves) can be included in the cartridge design to control fluid flow. These valves are actuated, in some embodiments, by corresponding hardware and software components in the measurement system.

The surface properties and texture of the cartridge surfaces in direct contact with the sample can be optimized to promote sample adhesion and/or sample flow. In some embodiments, the test chamber's interior surface and/or other interior surfaces of the fluidic circuit within the cartridge apparatus are plasma treated to optimize the surface energy and texture for adhesion of specific plasma proteins. In other embodiments, test chamber's interior surface and/or other interior surfaces of the fluidic circuit are treated with surface roughness texturing, material coating (such as in the case of gold plating), biological material coating (such as in the case of fibronectin or collagen coating, for example), raw material selection (e.g., use of specific plastic or other materials for the plate that does not require additional treatment), etc. Such treatments maybe performed independently, or in conjunction with, a plasma treatment. Similarly, the cartridge materials can be selected or manipulated to achieve the desired hydrophobicity or hydrophilicity. These properties can be changed by plasma treatment or by surface coatings.

As described in more details below, the cartridge and the associated measurement system can utilize one or more sensors of one or more types (e.g., optics, pressure, ultrasound, etc.) as part of the automated operations of the cartridge. In addition, the outputs of such one or more sensor(s) can be further utilized to perform quality control checks. These checks may be performed before, during, or after cartridge testing to ensure function of one or more of the subsystems (for example, ultrasound or other interrogation system, fluidics, fluid level, clamping, cartridge positioning/orientation system, or temperature control), ensure the cartridge is functional, ensure correct sample preparation before measurements are performed or have been performed for the measurement, and may also be used to accept or reject a test result or even to abort testing before initiation of measurements.

Note that in the discussion below a fluidic circuit includes a channel with fluidic component that connects one or more chambers together. Fluid circuit is also referred to as a testing channel in a multitude of channels that can be individually and controllably processed within a single cartridge apparatus.

Cartridge Input Section

Figure 2:
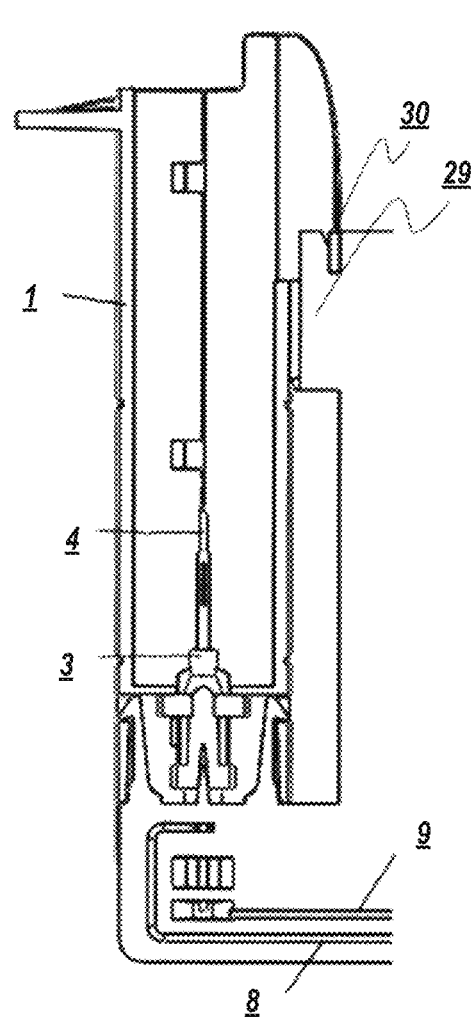
FIG. 2 shows a side cross-sectional view of the example biological sample input of FIG. 1 with a casing, in accordance with an illustrative embodiment.
Figure 3:
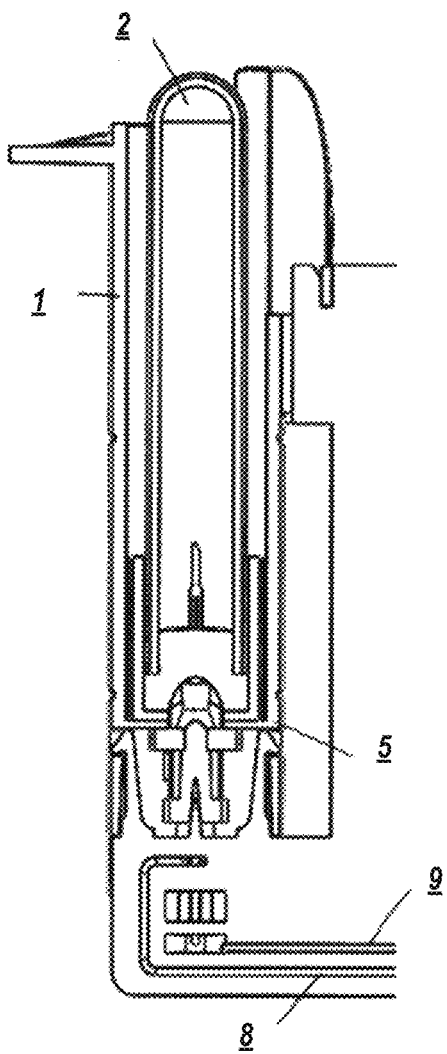
FIG. 3 shows a side cross-sectional view of the example biological sample input of FIG. 2 with a sample holding tube attached thereon, in accordance with an illustrative embodiment.
Figure 4:
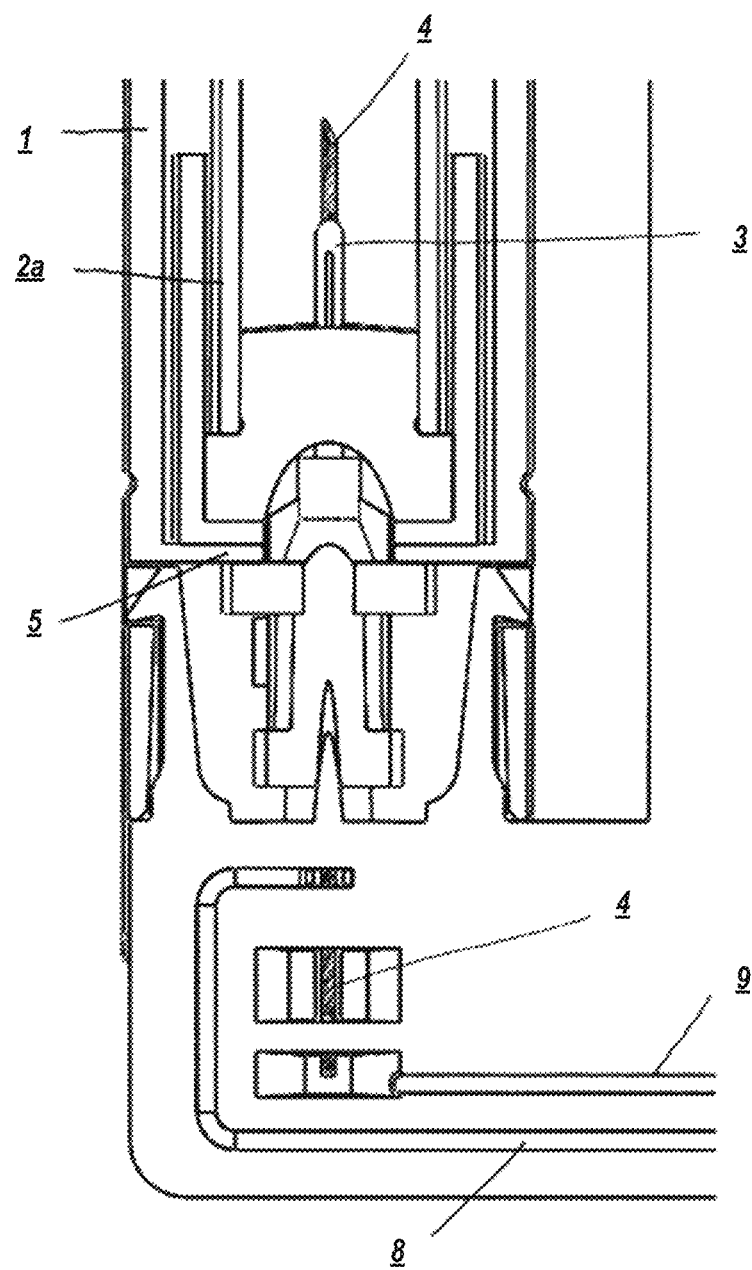
FIG. 4 shows a detailed view of the example biological sample input of FIG. 3, in accordance with an illustrative embodiment.

FIGS. 1, 2, 3, and 4 are schematic illustrations of an example biological sample input section of a cartridge 100 for evaluating hemostasis. Specifically, FIG. 1 shows a perspective view of an example biological sample input of a cartridge for use in disposable system, in accordance with an illustrative embodiment. FIG. 2 shows a side view of the example biological sample input of FIG. 1 with a casing, in accordance with an illustrative embodiment. FIG. 3 shows a side cross-sectional view of the example biological sample input of FIG. 2 with a sample holding tube attached thereon, in accordance with an illustrative embodiment. FIG. 4 shows a detailed view of the example biological sample input of FIG. 3, in accordance with an illustrative embodiment. In alternative embodiments, the input section of the cartridge comprises a well to which fluid sample can be placed, for example, by way of a pipette or tube.

In some embodiments, and as shown in FIG. 1, the cartridge 100 has a dual connection tab 28*a*, 28*b* for coupling the cartridge 100 to a sample container guide 1 (shown in FIG. 2). As shown in FIG. 2, the sample container guide 1, when mated with the cartridge 100, aligns a sample container 2 to a sample input port 3 of the cartridge 100. The cartridge 100 also includes an alignment tab 29 that is configured to slide into an alignment groove 30 of the sample container guide 1 to further stabilize the coupling of the sample container guide 1 to the cartridge 100. The sample container guide 1 can further provide a hard stop 5 (shown in FIG. 3) to hold the sample container 2 at the appropriate height to establish fluidic communication with the cartridge 100.

In various embodiments, the sample container 2 is an evacuated tube (also referred to herein as the sample holding tube 2) such as a BD Vacutainer™ tube, and the sample input port 3 comprises one or more needles required for sample transferring 3*a* and venting 4 (see FIG. 1). Though shown as concentric in the figures, the needles can be configured to be concentric, side by side, or integrated. In some embodiments, and as shown in FIG. 1, the sample transferring needle 3*a* includes inlets (3*b* and 3*d*) and an outlet 3*c* that terminates in a sample inlet chamber 26 of the cartridge 100. The sample inlet chamber 26 is in fluid communication with an inlet pathway 8 that leads to a retention/heating chamber 6 (see FIG. 5A). In some embodiments, and as shown in FIG. 1, the venting needle 4 includes an outlet 4*a* that is configured to terminate within the sample container 2 when attached and is spaced apart from the inlet 3*d* so as to minimize bubbles being drawn into the inlets 3*b* and 3*d*. The venting needle 4 also has an inlet 4*b* that terminates in a venting inlet chamber 27 of the cartridge. The venting inlet chamber 27 is in fluid communication with a vent pathway 9 that, in some embodiments, terminates at a filter chamber 9a (shown in FIG. 5A) housing a filter. An alternative sample container 2 can be utilized, such as a syringe, which requires a luer lock connection on the cartridge 100. And, as noted above, in other embodiments, the input section of the cartridge comprises a well to which fluid sample can be placed, for example, by way of a pipette or tube.

Vent Pathway

Figure 5A:
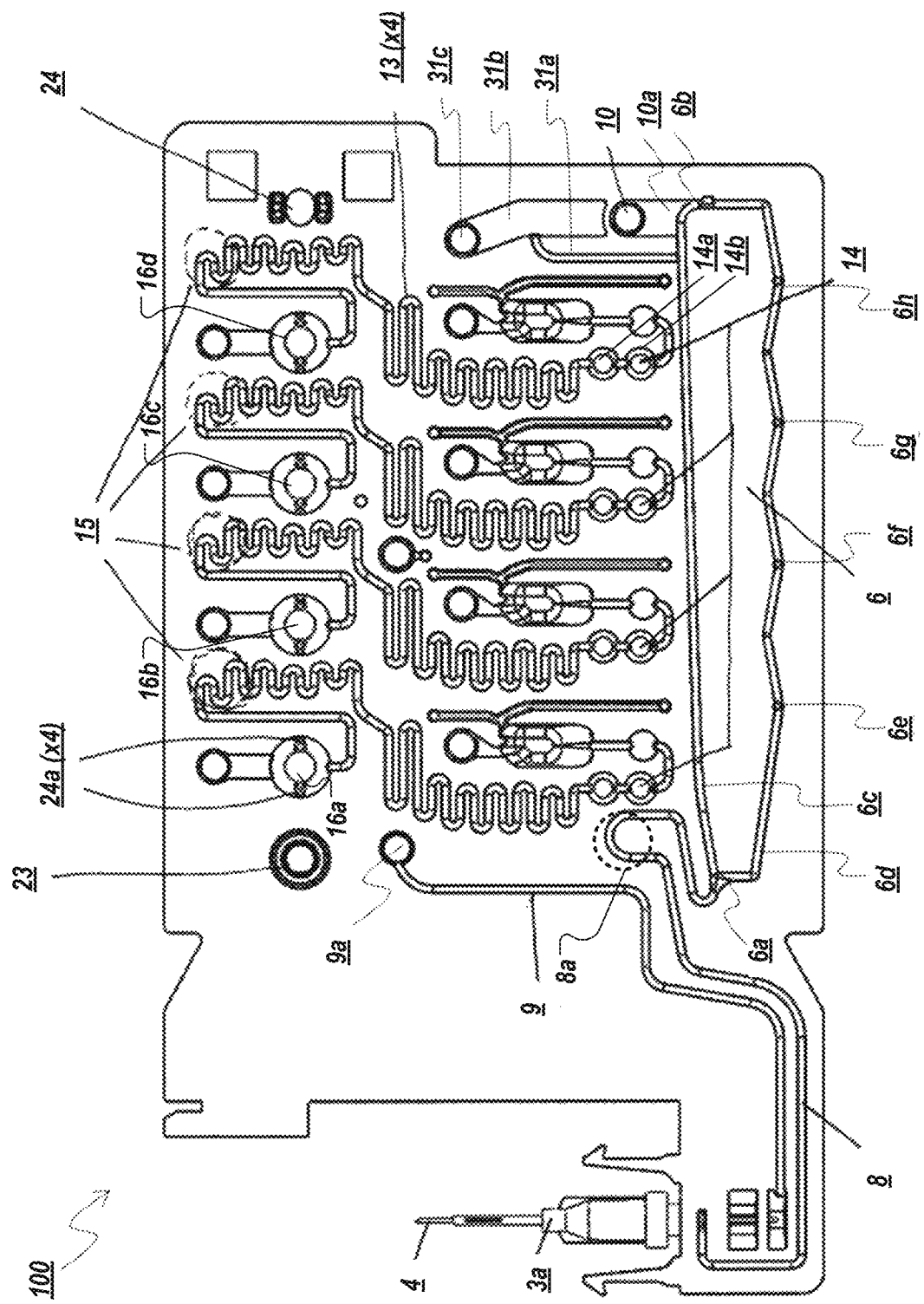
FIGS. 5A and 5B each shows the biological fluid pathways of four testing circuits (e.g., Hemostasis testing circuits) that are located on a sample preparation plane, in accordance with an illustrative embodiment.
Figure 5B:
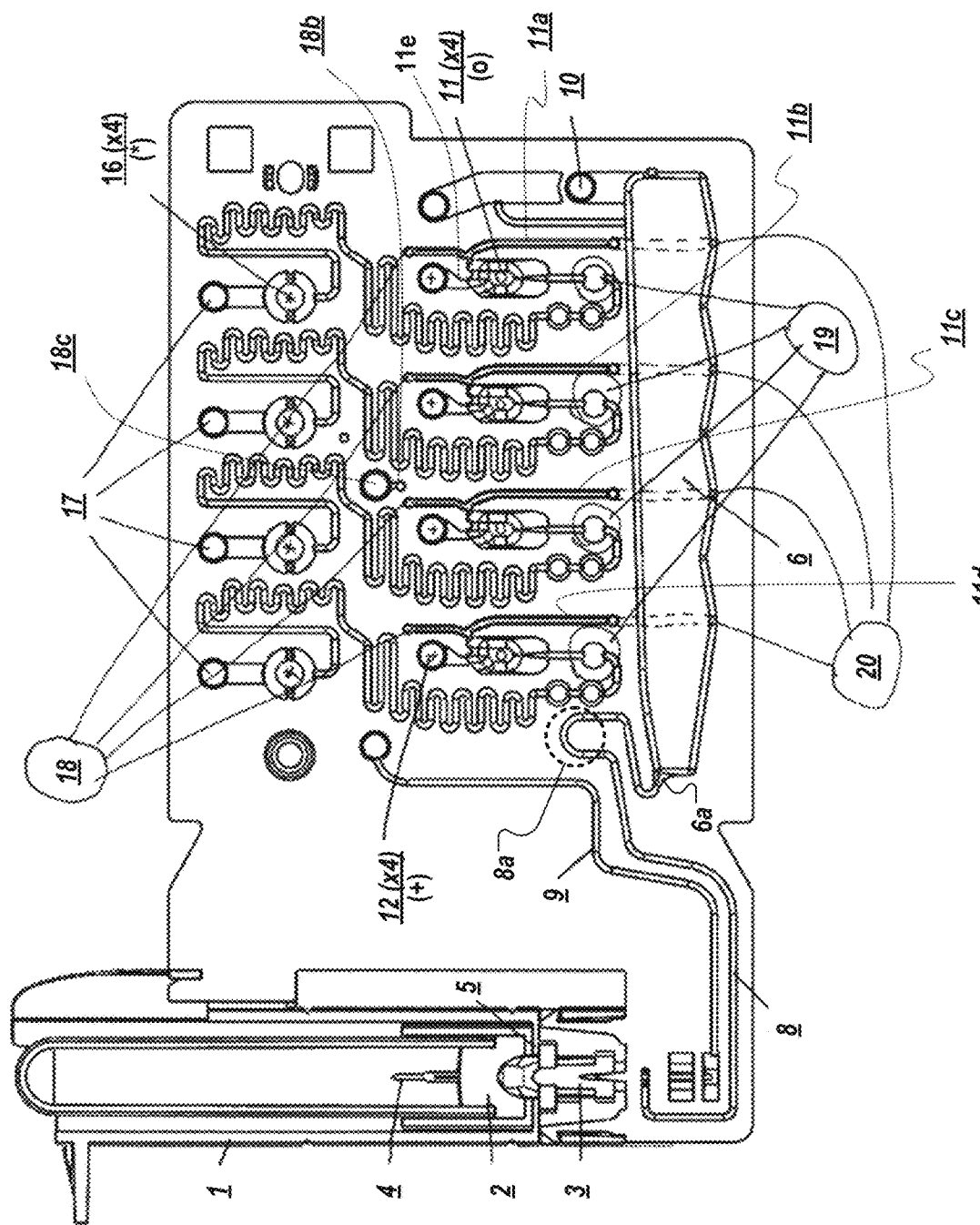
Figure 7:
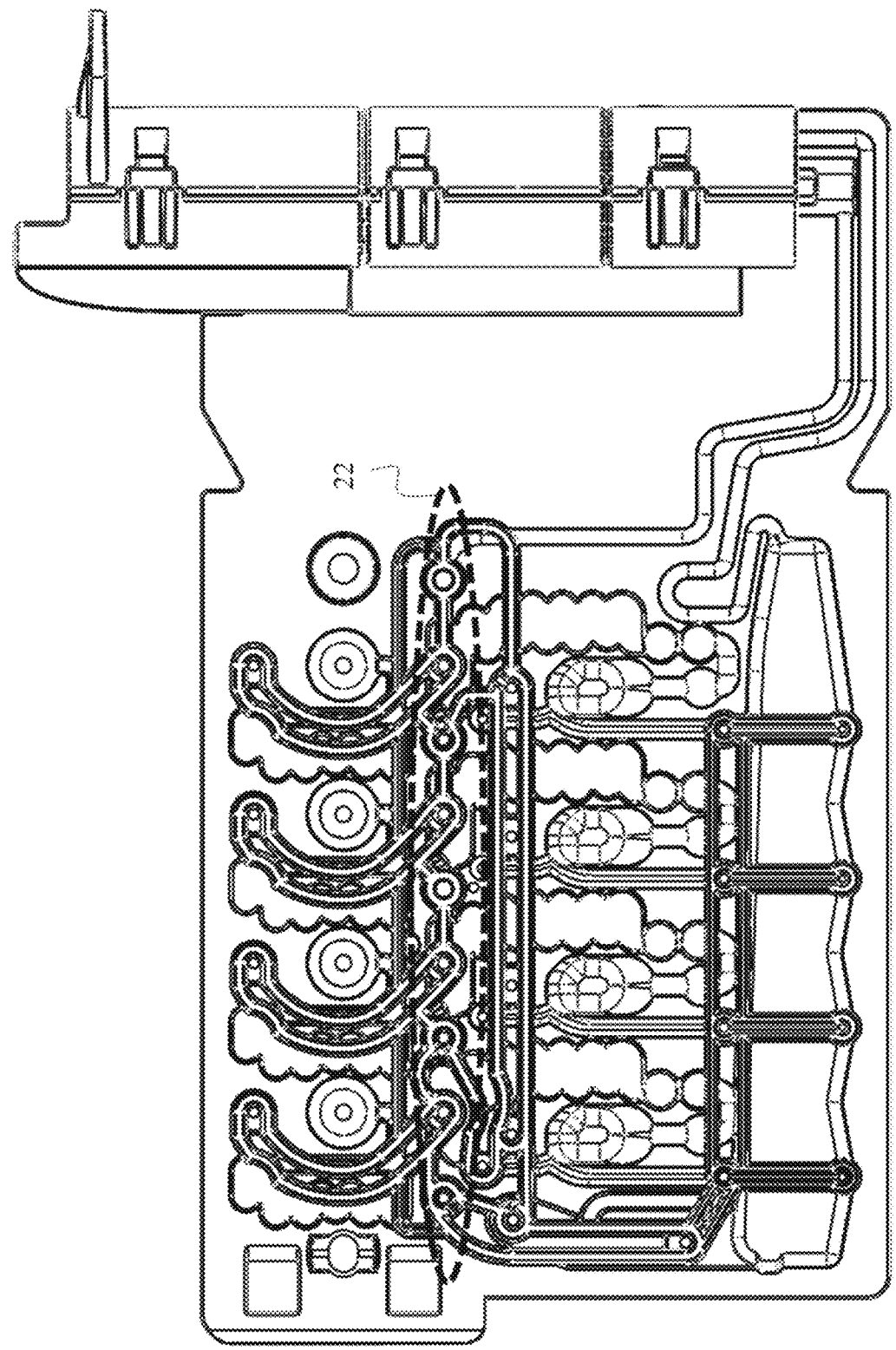
FIG. 7 shows the back-side of the cartridge of FIG. 5A and includes an interconnection plane that interfaces to the sample preparation plane, that collectively form the biological fluid pathways for the testing circuits, in accordance with an illustrative embodiment.
Figure 8:
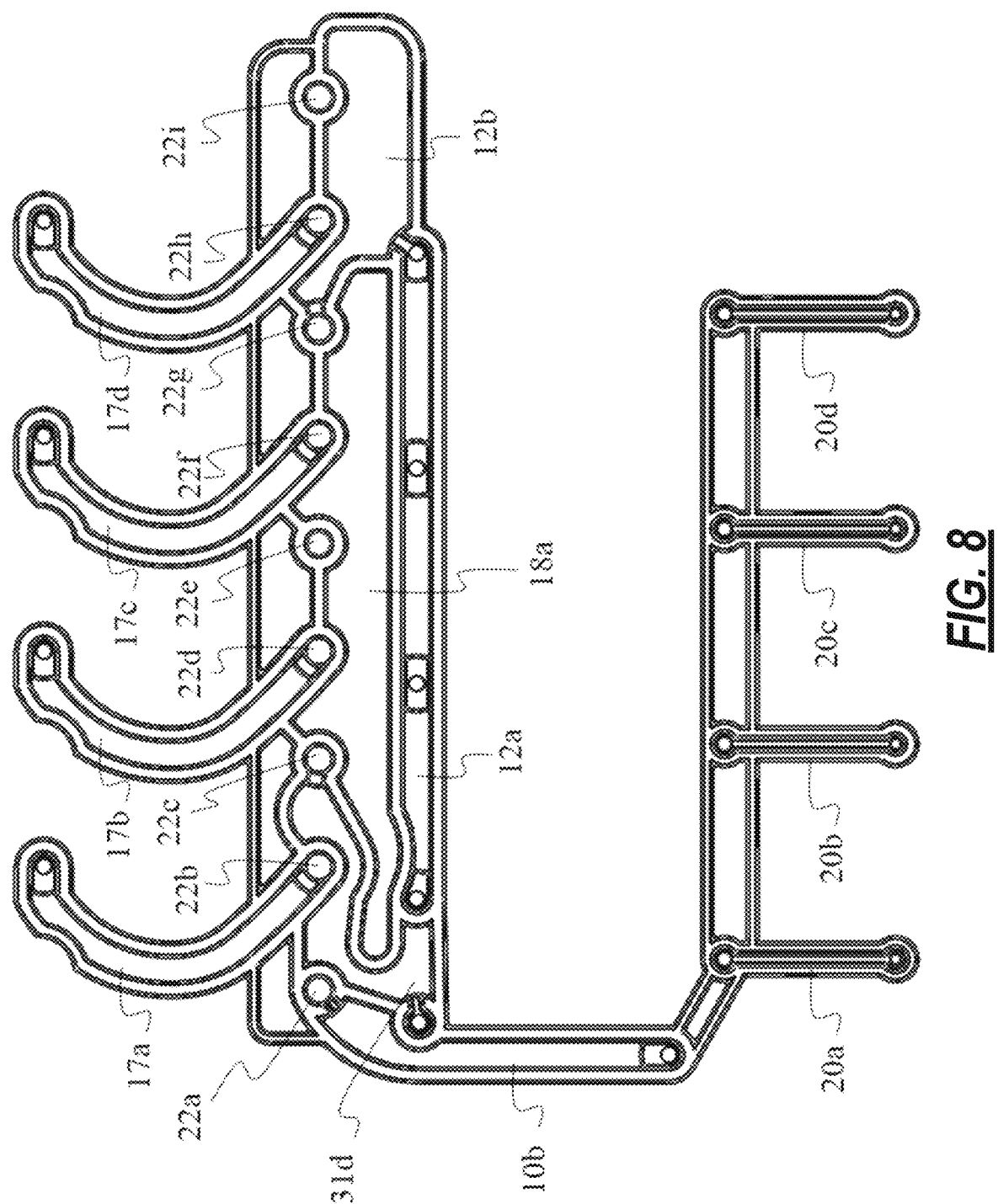
FIG. 8 shows portions of the biological fluid pathways that are on the interconnection plane of FIG. 7, in accordance with an illustrative embodiment.

FIGS. 5A, 5B, 7, and 8 are schematic illustrations of biological fluid pathways of the example cartridge 100 in accordance to an embodiment. Specifically, FIGS. 5A and 5B each shows the biological fluid pathways of four testing circuits (corresponding to test chambers 16a, 16b, 16c, and 16d, shown in FIG. 5A), also referred to herein as Hemostasis testing circuits, that are located on a sample preparation plane, in accordance with an illustrative embodiment. Though shown with four testing circuits, additional circuits or less may be included, including, e.g., two, three, five, six, seven, eight, and etc. FIG. 5B further shows of the cartridge body of FIG. 5A further coupled to a sample holding tube 2, in accordance with an illustrative embodiment. FIG. 7 shows the back-side of the cartridge of FIG. 5A and includes an interconnection plane that interfaces to the sample preparation plane, that collectively form the biological fluid pathways for the testing circuits, in accordance with an illustrative embodiment. FIG. 8 shows portions of the biological fluid pathways that are on the interconnection plane of FIG. 7, in accordance with an illustrative embodiment.

As noted above, the biological fluid pathways are formed on, and across, multiple planes defined in the cartridge 100. A first plane of fluid pathways of the cartridge 100 is shown in FIGS. 5A and 5B. The first plane of fluid pathways of the cartridge 100 may alternatively be referred to as a front plane of the cartridge 100. FIGS. 7 and 8 each shows a second plane of fluid pathways of the cartridge 100 in which FIG. 8 shows the fluid pathways in the second plane isolated from the remainder of the structure of the cartridge 100 for ease of understanding. The second plane of fluid pathways of the cartridge 100 may alternatively be referred to as a back plane of the cartridge 100. The fluid pathways between the first and second planes are connected by fluidic vias that traverse across the various planes of the cartridge 100.

As discussed above in relation to FIG. 1, in some embodiments, the venting inlet chamber 27 is in fluid communication with a vent pathway 9. The vent pathway 9 may terminate at a filter chamber 9a (shown in FIG. 5A), which may house a filter therein. The filter chamber 9a in the first plane of fluid pathways of the cartridge 100 is in fluid communication with a vent port 22i (shown in FIG. 8) in the second plane of fluid pathways of the cartridge 100. As discussed in more detail below, cartridge 100 couples with the measurement system (also referred to herein as the instrument) via the vent port 22i to provide atmospheric pressure to vent pathway 9.

Heating Chamber Pathway

As discussed above in relation to FIG. 1, in some embodiments, the sample transferring needle outlet 3c terminates in a sample inlet chamber 26 of the cartridge 100. The sample inlet chamber 26 is in fluid communication with an inlet pathway 8. The sample inlet pathway 8 provides a fluid communication pathway between the sample inlet chamber 26 and a retaining/heating chamber 6 (also referred to herein as heating chamber 6 or as a "first chamber") (shown in FIG. 5A). The label "first", "second", and "third" as used herein is provided merely as labels and do not intended to connote a sequence. The heating chamber 6 is configured to mate with a corresponding thermal regulating (e.g., heating/cooling) system in the measurement system to warm or cool the sample toward or to, or near, a pre-defined temperature.

The heating chamber 6, as provided herein, facilitate uniform conditioning of the test fluid prior to the fluid be metered or aliquoted to their respective testing, thus reducing variability in the test sample that can affect subsequent measurements and analysis. The shape of the heating chamber 6 can be optimized for heating/cooling transfer, as in the case here in which a thin cross-section with thin walls is used. The materials of the cartridge 100 can also be optimized to facilitate heating/cooling. In some embodiments, the sample heating/cooling conditioning stage can also be implemented in one or more chamber/channels of the cartridge design and it is not limited to just occur within just the heating chamber 6. In some embodiments, a stirring, rotating, or oscillating element (not shown) can be placed in the heating chamber 6 that may be controlled by the measurement system to promote uniform temperature heating or cooling. In other embodiments, test fluid in the heating chamber 6 may be vibrated by the measurement system vibrating the cartridge 100 to promote uniform temperature conditioning of the test fluid.

In some embodiments, temperature measurement is conducted of the test sample in the cartridge 100. To measure the temperature, a sensor can be incorporated in the measurement system or in the cartridge 100. In some embodiments, a thermistor or thermocouple can be placed in physical contact with the cartridge 100, or biological sample (such as blood). In other embodiments, an IR thermometer is pointed at the cartridge 100 or biological sample. In either case the cartridge 100 may incorporate a small well through which the incoming blood passes, rather than having direct contact with the blood. In some embodiments, the temperature of the test sample may be assessed at or near the heating chamber 6. In other embodiments, the temperature of the test sample may be assessed while the test sample is flowing through channels as it is directed toward the test chambers 16.

Referring now to FIGS. 5A, 5B, and 8, the sample inlet pathway 8 terminates at a first corner 6a of the heating chamber 6, shown as the top left corner of heating chamber 6 in FIGS. 5A and 5B. In some embodiments, chambers along the fluid pathways are generally filled from the top as to prevent blood to backflow into the inlet. A fill outlet channel 10a extends from a second corner 6b of the heating chamber 6 opposite from the first corner 6a.

Figure 6A:
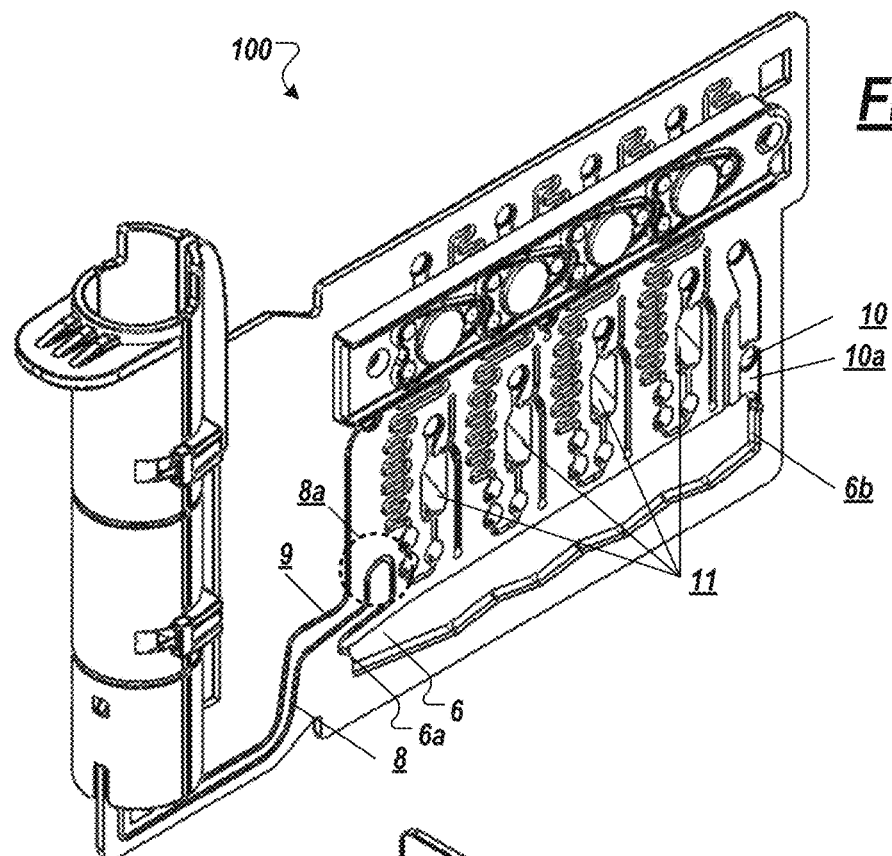
FIGS. 6A and 6B show a front perspective view and a back perspective view of FIGS. 5A, 5B, and 8 with labels corresponding to the heating chamber filling.
Figure 6B:
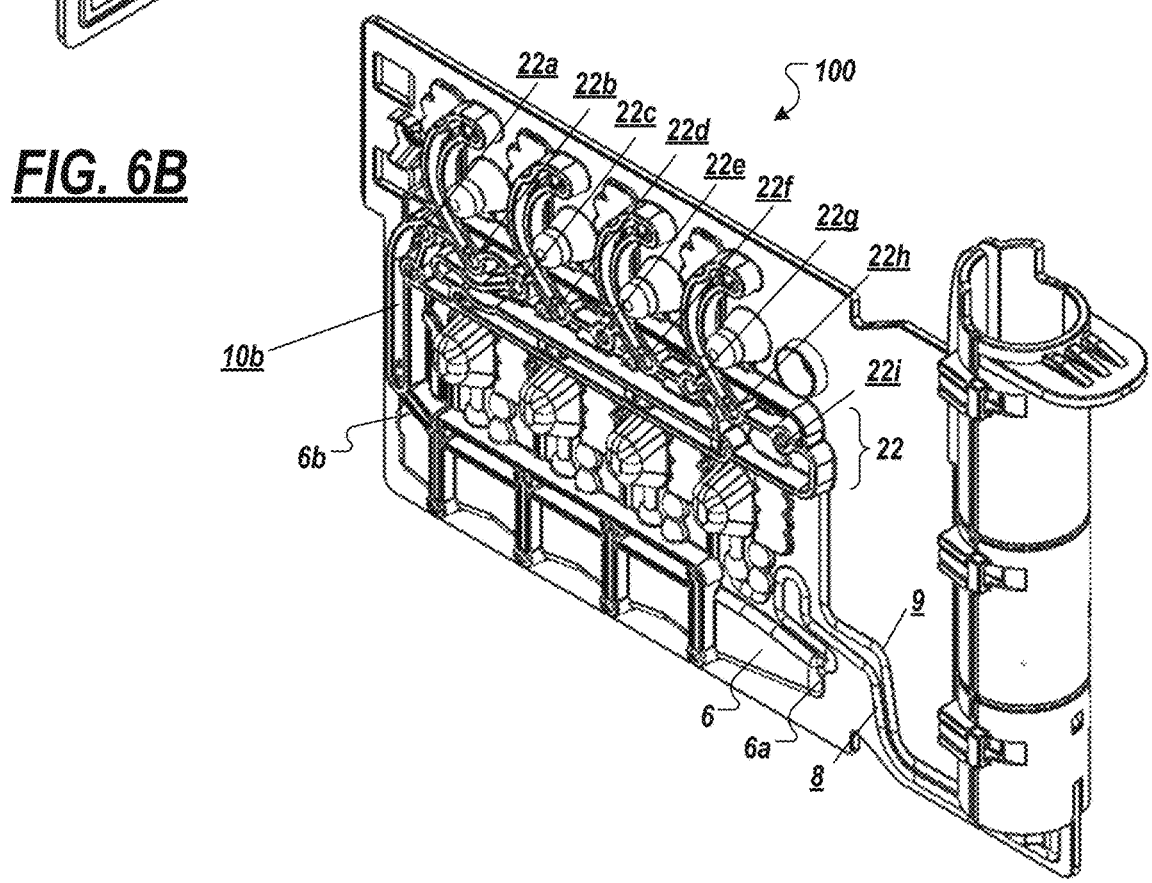

The fill outlet channel 10a extends to a filter chamber 10 with a filter therein. The filter chamber 10 (e.g., as shown in FIGS. 5A and 5B) in the first plane of fluid pathways of the cartridge 100 is in fluid communication with a heating-chamber fill channel 10b shown in the second plane of fluid pathways of the cartridge 100 (see FIG. 8). The fill conduit 10b is in fluid communication with a pressure port 22a (see also FIG. 8) that facilitate filling of the heating chamber 6. The conduit 10b is a part of a network of conduits used to consolidate pressure ports (e.g., 22a as discussed, as well as 22b-22i to be later discussed) of the cartridge 100 to one or more areas to which the measurement system can coupled with its pressure control interfaces. Such configuration reduces the complexity of the measurement system to control fluid movement within the cartridge 100. Indeed, the conduits that handles the control of movement of the fluid sample in the first plane of the cartridge 100 is primarily placed in the second plane of the cartridge 100. FIGS. 6A and 6B show a front perspective view and a back perspective view of FIGS. 5A, 5B, and 8 with additional labels corresponding to the description of this section.

Heating Chamber Fill

In operation, the instrument's fluid pump aspirates the sample through the input port 3 (see FIGS. 1-2) via the connection ports 22 (see FIG. 7) (also referred to herein as pressure ports) and into the heating chamber 6 (see FIG. 5A or 5B) of the cartridge 100. For example, the instrument's fluid pump may be in communication with and apply differential pressure (e.g., positive or negative) to a pressure port 22a (see FIG. 8). This in turn creates an applied pressure along the fill conduit 10b, within the heating chamber 6, and along the inlet pathway 8 to aspirate the sample into the heating chamber 6. At the same time, the inner vent needle 4 is linked to the isolated pathway 9 that receives atmospheric pressure from the instrument via the vent port 22i (see FIG. 8) to neutralize pressure in the sample container 2 as the sample is aspirated into the heating chamber 6 of the cartridge 100. During filling of the heating chamber 6, all other ports (e.g., 22b-22l) are closed, e.g., by the measurement system.

When the heating chamber 6 is filled, the filter within filter chamber 10 is clogged and creates a pressure spike that is detected by the instrument, causing the instrument to turn off the fluidic pump. The instrument may also close the vent port 22i or otherwise discontinue supplying atmospheric pressure via vent port 22i upon detecting the pressure spike. Alternative filling detection techniques could also be used, i.e., optical sensors placed at the desired fill level, volumetric control, fixed time of pressure alteration (negative and/or positive pressures), ultrasound detectors placed at the desired fill level, etc. The sample remains in the heating chamber until the desired temperature is reached, which can for example be at or near body temperature of a normal and typical subject (e.g., about 37° C. for a healthy person). In other instances, other desired temperatures may be warranted. The shape of the heating chamber 6 and the channels leading to the sample metering chambers 11 (described below) are configured so that bubbles that might be present in the fluid sample are trapped away from the rest of the fluidic circuit. The shape of the inlet pathway 8 includes an anti-siphon feature 8a (see FIGS. 5A and 5B) and is configured to reduce the occurrence of bubbles forming in the heating chamber 6 and prevent siphoning to and from the sample container 2. To this end, additional unprocessed test sample (e.g., un-warmed blood) is prevented from being siphoned into the heating chamber following the first drawn test sample being heated and/or cooled, e.g., when the processed test sample is pulled into the metering chamber 11 (also referred to herein as sample chamber 11 and "second" chamber). FIGS. 6A and 6B also show labels corresponding to the description of this section.

Sample Aliquot (Metering) Chambers Pathway

Referring to FIGS. 5A, 5B, and 8, a first side 6c of the heating chamber 6 (see FIG. 5A) extends between the first corner 6a and the second corner 6b.

One or more of outlet ports 6e-6h (see FIG. 5A) are arranged along the length of the second side 6d of the heating chamber. Each of the one or more outlet ports 6e-6h may be arranged in a different one of the valleys along the second side 6d of the heating chamber in which the valleys direct the sample into conduits leading to each respective test channel. A test channel, in some embodiments, refers to the associated fluidic pathway structures and testing chamber, collectively, used to perform a measurement for a given aliquot sample. In some embodiments, and as shown in FIG. 5B, each of the one or more outlet ports 6e-6h in the first plane of fluid pathways of the cartridge 100 is in fluid communication with a first end of a corresponding one or more channels 20a-20d (see FIG. 8) in the second plane of fluid pathways of the cartridge 100, collectively referred to as channels 20 (see FIG. 5B). A second end of each of the one or more channels 20a-20d (see FIG. 8) in the second plane of fluid pathways of the cartridge 100 is likewise in fluid communication with a first end of a corresponding one or more channels 11a-11d (see FIG. 5B) in the first plane of fluid pathways of the cartridge 100. A second end of each of the one or more channels 11a-11d terminates in a corresponding one or more sample chambers 11 (shown in duplicates ("×4") in FIG. 5B with an "o" symbol therein). In the example shown in FIGS. 5A, 5B, 7, and 8, there are four sample chambers 11. More or fewer sample chambers 11 and corresponding fluid communication pathways with the heating chamber 6 may be present on the cartridge 100 in some configurations.

The sample chambers 11 are fed by the one or more channels 20 originating from the bottom of the heating chamber 6. This geometric configuration avoids bubbles being drawn into the sample chambers 11 as the bubbles rise to the upper portion of the heating chamber 6.

Each of the sample chambers 11 has a corresponding fill channel 11e that is in fluid communication with a corresponding filter chamber 12 (shown in duplicates ("×4") in FIG. 5B with a "+" symbol) with a filter therein. The filter chamber 12 in the first plane of fluid pathways of the cartridge 100 is in fluid communication with a channel 12a (see FIG. 8) in the second plane of fluid pathways of the cartridge 100. The channel 12a is in fluid communication with a pressure port 22g (see FIG. 8).

Figure 6C:
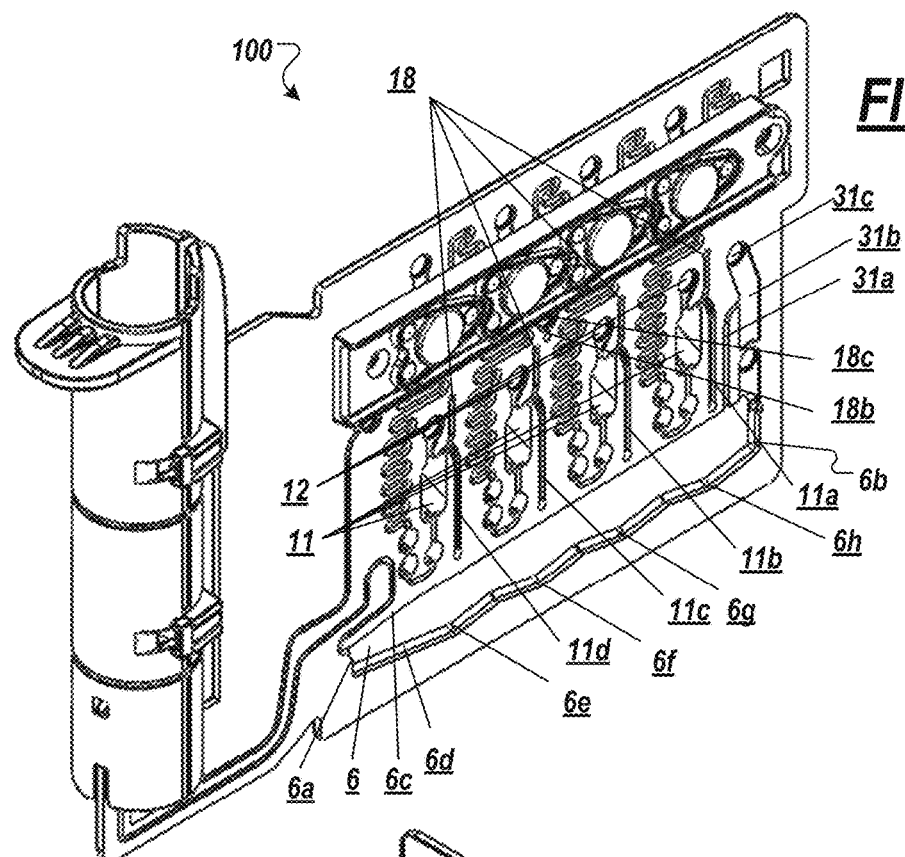
FIGS. 6C and 6D show a front perspective view and a back perspective view of FIGS. 5A, 5B, and 8 with labels corresponding to the sample chamber filling.
Figure 6D:
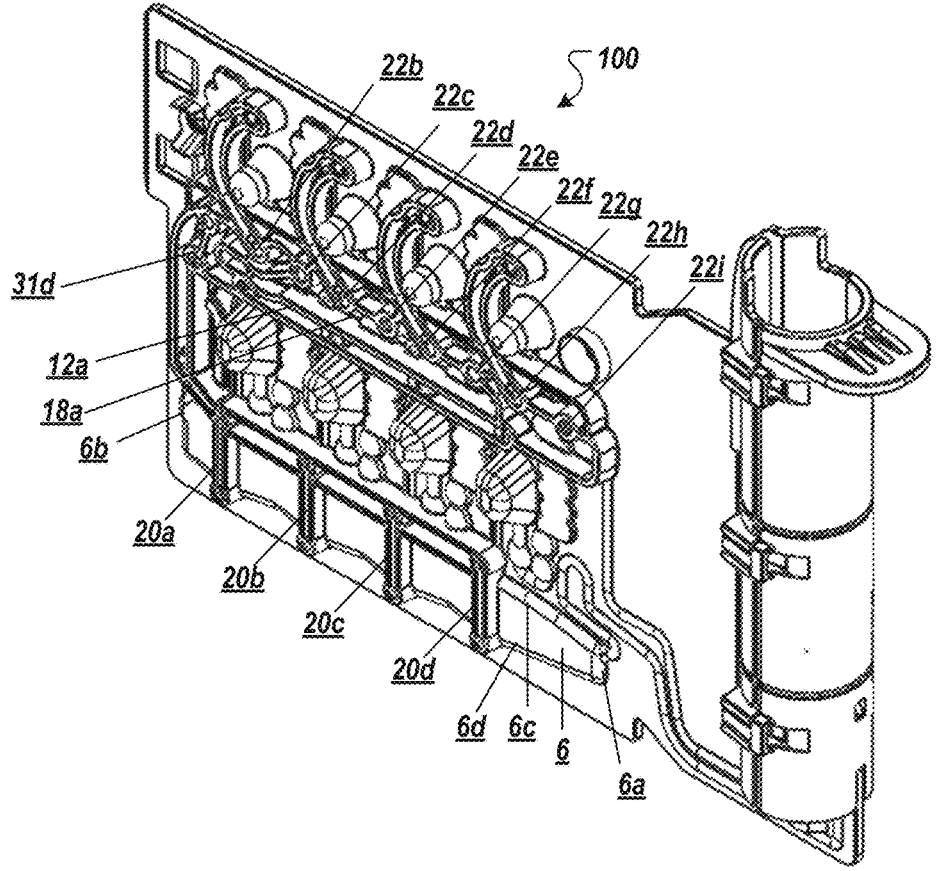

In some configurations, when more than one sample chamber 11 are implemented on the cartridge 100, the channel 12a (see FIG. 8) is in fluid communication with all of the sample chambers 11 (see FIG. 5B) via corresponding fill channels 11e and filter chambers 12. Accordingly, channel 12a acts as a manifold for applying negative pressure to all of the sample chambers 11 via a single pressure port 22g. Therefore, a separate pressure port is beneficially not needed for filling each of the sample chambers 11. FIGS. 6C and 6D show a front perspective view and a back perspective view of FIGS. 5A, 5B, and 8 with additional labels corresponding to the description of this section.

Heating Chamber Vent Pathway

Referring to FIGS. 5A, 5B, and 8, the heating chamber 6 comprises a vent pathway 31a, 31b, 31c along the first side 6c of the heating chamber for venting the heating chamber 6 as the sample chambers 11 are filled. The vent pathway 31 (not shown) includes the fluid pathway through conduit elements 31a-31d. Channels 31a-31b terminate at one end in the heating chamber 6 along the first side 6c and terminate at the other end at a filter chamber 31c with a filter therein. Accordingly, channels 31a-b provide a fluid pathway between the heating chamber 6 and the filter chamber 31c. The filter chamber 31c (see FIG. 5A) in the first plane of fluid pathways of the cartridge 100 is in fluid communication with a channel 31d (see FIG. 8) in the second plane of fluid pathways of the cartridge 100, which in turn is in fluid communication with a vent port 22c (see FIG. 8). As discussed in more detail below, cartridge 100 couples with the instrument via the vent port 22c for the instrument to provide atmospheric pressure to vent the heating chamber 6. FIGS. 6C and 6D also show labels corresponding to the description of this section.

Sample Chamber Vent Pathway

Referring to FIGS. 5A, 5B, and 8 each of the sample chambers 11 includes a vent pathway 18 that terminates at a first end in a corresponding sample chamber 11. A second end of the vent pathway 18 in the first plane of fluid pathways of the cartridge 100 is in fluid communication with a vent manifold 18 in the second plan of fluid pathways of the cartridge 100. When more than one sample chamber 11 is present, all of the vent pathways 18 (see FIG. 5B) of the sample chambers are in fluid communication with the vent manifold 18a (see FIG. 8). The vent manifold 18a (see FIG. 8) in the second plane of fluid pathways of the cartridge 100 is further in fluid communication with a first end of a channel 18b (see FIG. 5B) in the first plane of fluid pathways. A second end of channel 18b (see FIG. 5B) is in fluid communication with a filter chamber 18c (see FIG. 5B) with a filter therein. Filter chamber 18c (see FIG. 5B) in the first plane of fluid pathways of the cartridge 100 is in fluid communication with a vent port 22e (see FIG. 8). FIGS. 6C and 6D also show labels corresponding to the description of this section.

Sample Aliquot (Metering) Chambers Fill

During operation, once the sample is at, or near, the desired temperature, the sample is aliquoted (or metered) into one or more independent sample chambers 11 (see FIG. 5B). Referring to FIG. 5B unless indicated otherwise, in various embodiments, the sample chambers are filled by applying a negative pressure at pressure port 22g (see FIG. 8) via a pump in the instrument while venting the heating chamber 6 by way of the vent port 22c (see FIG. 8). Each filter chamber 12 has a filter therein that will clog when the corresponding sample chamber 11 is filled and will trigger the pressure sensor of the instrument to turn the pump off, similar to filling the heating chamber 6. As discussed above, alternative filling detection techniques could be used. In various embodiments, all the sample chambers 11 are controlled by a single valve and fluidic pathway in the instrument via pressure port 22g (see FIG. 8). The cutoff pressure will not trigger until all sample chambers' filters clog in the corresponding filter chambers 12. The sample chambers 11 are used to separate samples into independent functional channels, aliquot a known volume of sample, and stage the sample for mixing with reagents. While the sample chambers 11 are filled, pressure ports 22b, 22d, 22f, and 22h (see FIG. 8) as well as vent port 22e (see FIG. 8) are closed by the instrument so as to prevent fluid from leaking past the location 19, arranged below the sample chambers 11. Once the sample chambers 11 have been filled, the vent port 22e (see FIG. 8) is opened to atmospheric pressure so that the one or more sample chambers 11 can be fluidically separated from each other and the heating chamber 6. Vent port 22e (see FIG. 8) remains open to atmosphere during sample mixing as discussed below. FIGS. 6C and 6D also show labels corresponding to the description of this section.

Mixing and Testing Pathway

Figure 6E:
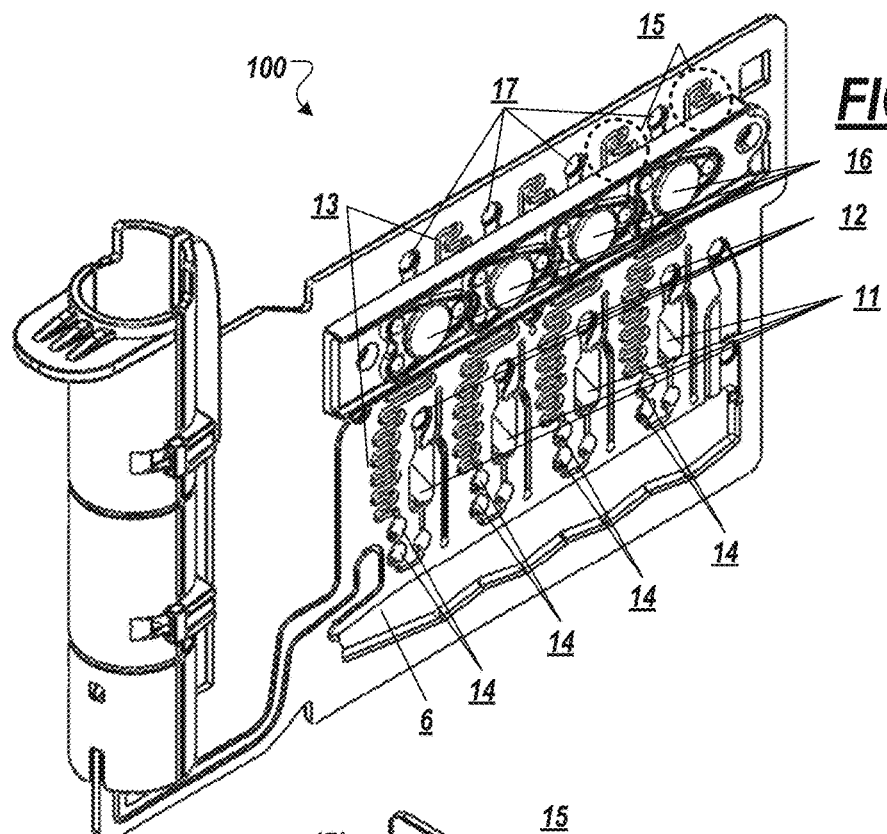
FIGS. 6E and 6F show a front perspective view and a back perspective view of FIGS. 5A, 5B, and 8 with labels corresponding to the sample mixing and test chamber filling.
Figure 6F:
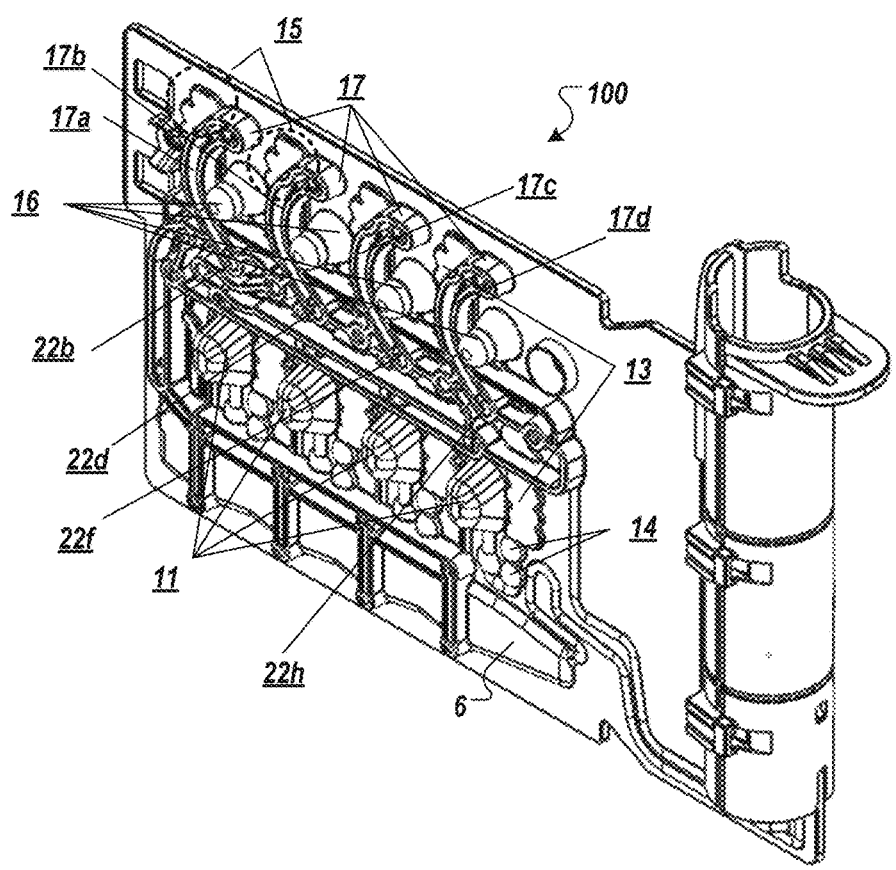

Referring to FIG. 5B unless indicated otherwise, each of the sample chambers 11 is in fluid communication with a corresponding one or more reagent pocket 14 (see FIG. 5A) configured to house at least one lyophilized bead comprising a reagent. As shown in FIGS. 5A and 5B, two reagent pockets 14 (shown as 14a and 14b in FIG. 5A for one of the test channels) are provided. In other embodiments, a single reagent pocket is used for each testing channel. In yet other embodiments, more than two reagent pockets 14 are used for each testing channel. The reagent pockets 14 are in turn in fluid communication with a serpentine channel 13 (see FIG. 5A, and shown with a duplication symbol ("×4"). Each of the serpentine channel 13 has a first end in fluid communication with the reagent pockets and a second end that terminates at an optical detection zone 15. As discussed below, the instrument (i.e., measurement system) may optically interrogate the optical detection zone 15 of the cartridge 100 to facilitate the control of a pump that facilitates mixing of the individual aliquots with the corresponding reagent(s). Each of the serpentine channel 13 (see FIG. 5A) is in fluid communication with a test chamber 16 (see FIG. 5B, with duplication symbol "×4") which in turn is in fluid communication with a filter chamber 17, with a filter therein. The filter chamber 17 in the first plane of fluid pathways of the cartridge 100 is in fluid communication with a first end of a corresponding one of fluid channels 17a-17d (see FIG. 8) in the second plane of fluid pathways of the cartridge 100. A second end of each of the fluid communication channels 17a-17d (see FIG. 8) are in fluid communication with a corresponding pressure port 22b, 22d, 22f, and 22h (see FIG. 8). The cartridge 100 couples with instrument via the pressure ports 22b, 22d, 22f, and 22h (see FIG. 8) to supply positive and negative pressure to facilitate mixing and testing of the sample as described below. FIGS. 6E and 6F also show a front perspective view and a back perspective view of FIGS. 5A, 5B, and 8 with additional labels corresponding to the description of this section.

Sample Mixing

Referring to FIG. 5B unless indicated otherwise, each individual aliquot in the sample chambers 11 is pulled into a separate reservoir or channel (a serpentine channel pathway 13 (see FIG. 5A) in various embodiments) and brought into contact with the channel specific reagent, located in one (or both) of the two reagent pockets 14 (see FIG. 5A). Specifically, a pump in the instrument applies negative pressure to pressure ports 22b, 22d, 22f, and 22h (see FIG. 8) to draw the sample through the reagent pockets 14 (see FIG. 5A) and serpentine channel pathway 13 (see FIG. 5A). The reagents and sample are kept separate from each other during sample chamber 11 filling so as to avoid reagents floating on the blood and getting trapped in the filter in filter chambers 12, as well as to ensure fluidic isolation of the one or more sample chamber 11 from the heating chamber 6. To this end, precise time of when the test sample is in contact with the reagents can be measured thereby facilitating accurate and precise clot time measurements (e.g., from when mixing begins). In addition, the reagents and test samples are kept separated from one another, in some embodiments, until all channels are metered to prevent undesired siphoning of test samples from other channels or from the unprocessed sample in the fluidic pathways. The sample is aspirated through the serpentine channel 13 (see FIG. 5A) until it triggers an optical sensor in the instrument (detection zone is top of serpentine channel near the optical detection zone 15 (see FIG. 5A)) which closes off the channel from the pump. Mixing in the serpentine channels or zones, or region, therein can be controlled by one or more independent valves and pathways that allow individual channel control. Alternative sensor techniques could be utilized: pressure, pass through optical sensors, ultrasound detection, time, volumetric control, etc. Once all the channels' optical sensors trigger, the pump reverses and applies positive pressure to pressure ports 22b, 22d, 22f, and 22h (see FIG. 8). The positive pressure pushes the biological sample, such as blood, down the serpentine path 13 (see FIG. 5A) for a designated time, or until a second set of optical sensors in the instrument is tripped (in an alternative embodiment). This process, to pull the sample up the serpentine path 13 (see FIG. 5A) to the optical detection zone where it is detected by an optical sensor of the instrument and push back for a given time, repeats until full sample mixing is achieved. FIGS. 6E and 6F also show labels corresponding to the description of this section.

Other sensors (e.g., impedance sensors), pressure sensor, and etc., may be used. Alternatively, additional sensors may be used to detect both ends of the optical detection zone. Alternate pathway geometries, obstructions to create turbulence, cycle numbers, and cycle speed are all design alternatives that can be used with varying test types to achieve optimal results. In alternative embodiments, mixing could be achieved with one or more ferromagnetic beads or bars placed within the cartridge and controlled by the instrument.

Test Chamber Filling

Referring to FIGS. 5A, 5B, and 8, one or more testing chambers 16 are filled after mixing is completed. Using one or more independent valves and pathways, each testing chamber 16 is filled with a sample via the application of pressure perturbations (negative and/or positive pressure) at pressure ports 22b, 22d, 22f, and 22h. Specifically, the instrument pump will apply negative pressure to pressure ports 22b, 22d, 22f, and 22h until all of the filters are clogged in the one or more filter chambers and cause a pressure spike to cause the instrument to turn the pump off, similar to filling the heating chamber 6. As discussed above, alternative filling detection techniques could be used. The testing chambers 16 have design features such as the ridges 24a which prevent the formation of bubbles in the testing chambers 16 during filling. Once filled, the instrument begins viscoelastic testing of the sample. FIGS. 6E and 6F also show labels corresponding to the description of this section.

In some embodiments, the cartridge apparatus includes, at least, four independent fluidic circuits configured with different sets of reagents for measurements (and/or sample preparation) to be performed in parallel. The measurements are performed per channel of the, at least, four channels of the cartridge. The measurement, in some embodiments, include viscoelastic properties such as a sample shear modulus. The measurement, in another embodiment, includes other properties such as viscosity, elastic modulus, or any other mechanical property of the sample, or combinations thereof.

Table 1 provides an example set of reagents and measurement parameters for use in an example cartridge apparatus (e.g., apparatus 100, among others). As shown in Table 1, Channel #1 in the example cartridge apparatus is interrogated to measure clot time of the test sample in the presence of kaolin, which is an activator of the intrinsic pathway of coagulation. As shown in Table 1, Channel #2 is interrogated to measure clot time of the test sample in the presence of kaolin and in further presence of heparinase I, which is a neutralizer of the anticoagulant heparin. As shown in Table 1, Channel #3 is interrogated to measure overall clot stiffness of the test sample in the presence of i) thromboplastin, which is an activator of the extrinsic pathway of coagulation, and ii) polybrene, which is a neutralizer of the anticoagulant heparin. As shown in Table 1, Channel #4 is interrogated to measure clot stiffness of the test sample with the same reagents as channel #3, but with the addition of abciximab (e.g., Clotinab® and/or ReoPro®), which is an inhibitor of platelet aggregation/contraction. As shown in Table 1, when the assay is configured to operate with citrated whole blood samples, calcium is added to all the reagent formulations.

TABLE 1

Reagents utilized in a preferred embodiment

| Channel # | Reagents | Measurement (units) |
|---|---|---|
| 1 | Kaolin, calcium, buffers and stabilizers | Clot time (Seconds) |
| 2 | Kaolin, heparinase I, calcium, buffers and stabilizers | Clot time (Seconds) |
| 3 | Thromboplastin, polybrene, calcium, buffers and stabilizers | Clot stiffness (hecto Pascals) |
| 4 | Thromboplastin, polybrene, abciximab (and/or cytochalasin D), calcium, buffers and stabilizers | Clot stiffness (hecto Pascals) |

Table 2 provides an additional example set of reagents and measurements for use in an example cartridge apparatus (e.g., apparatus 100, among others). As shown in Table 2, channel #2 includes an extrinsic pathway activator with inhibition of fibrinolysis by tranexamic acid (TXA). In addition to the measurements previously presented in Table 1, channels #2, channel #3, and channel #4 are interrogated to also measure clot stiffness changes, which, for example, can be related to the fibrinolytic process. In some embodiments, other channels can include reagents that inhibit fibrinolysis and can also be interrogated to measure clot stiffness changes. For example, channel #4 could also include TXA or other fibrinolysis inhibitor in order to measure clot stiffness in the absence of fibrinolysis.

TABLE 2

Reagents utilized in a preferred embodiment

| Channel # | Reagents | Measurement (units) |
|---|---|---|
| 1 | Kaolin, calcium, buffers and stabilizers | Clot time (Seconds) |
| 2 | Thromboplastin, polybrene, calcium, tranexamic acid, buffers and stabilizers | Clot stiffness (hectoPascals) and Clot stiffness change |
| 3 | Thromboplastin, polybrene, calcium, buffers and stabilizers | Clot stiffness (hecto Pascals) and clot stiffness change |
| 4 | Thromboplastin, polybrene, abciximab (and/or cytochalasin D), calcium, buffers and stabilizers | Clot stiffness (hecto Pascals) and clot stiffness change |

Figure 13:
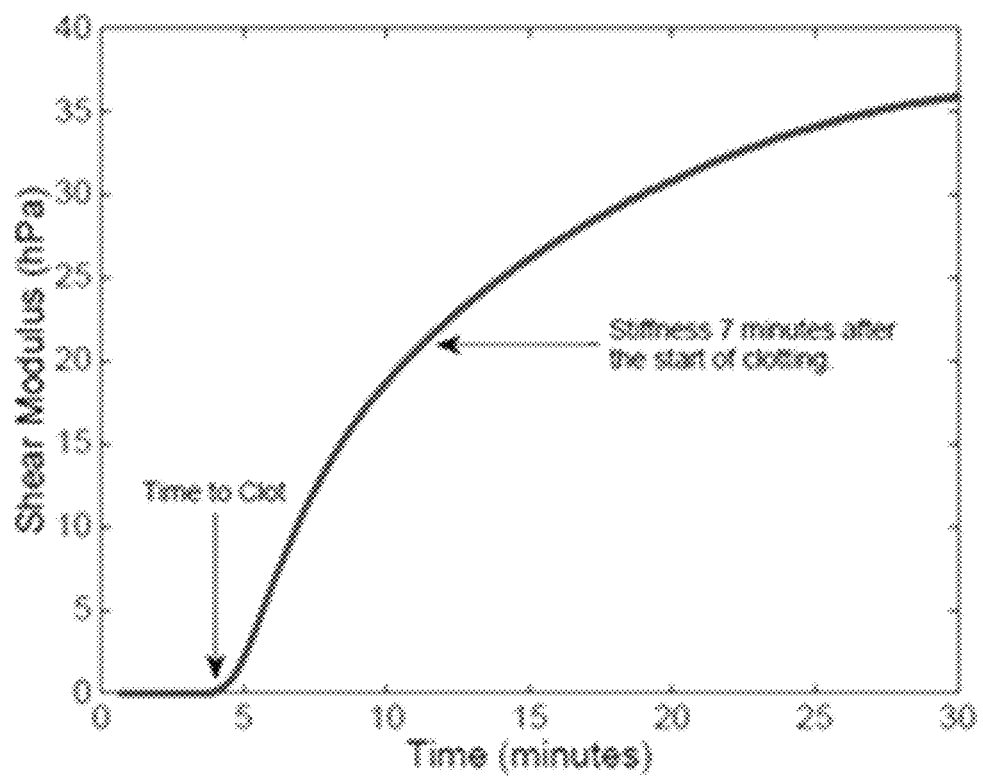
FIG. 13 shows an example shear modulus versus time curve, in accordance with an illustrative embodiment.
Figure 14:
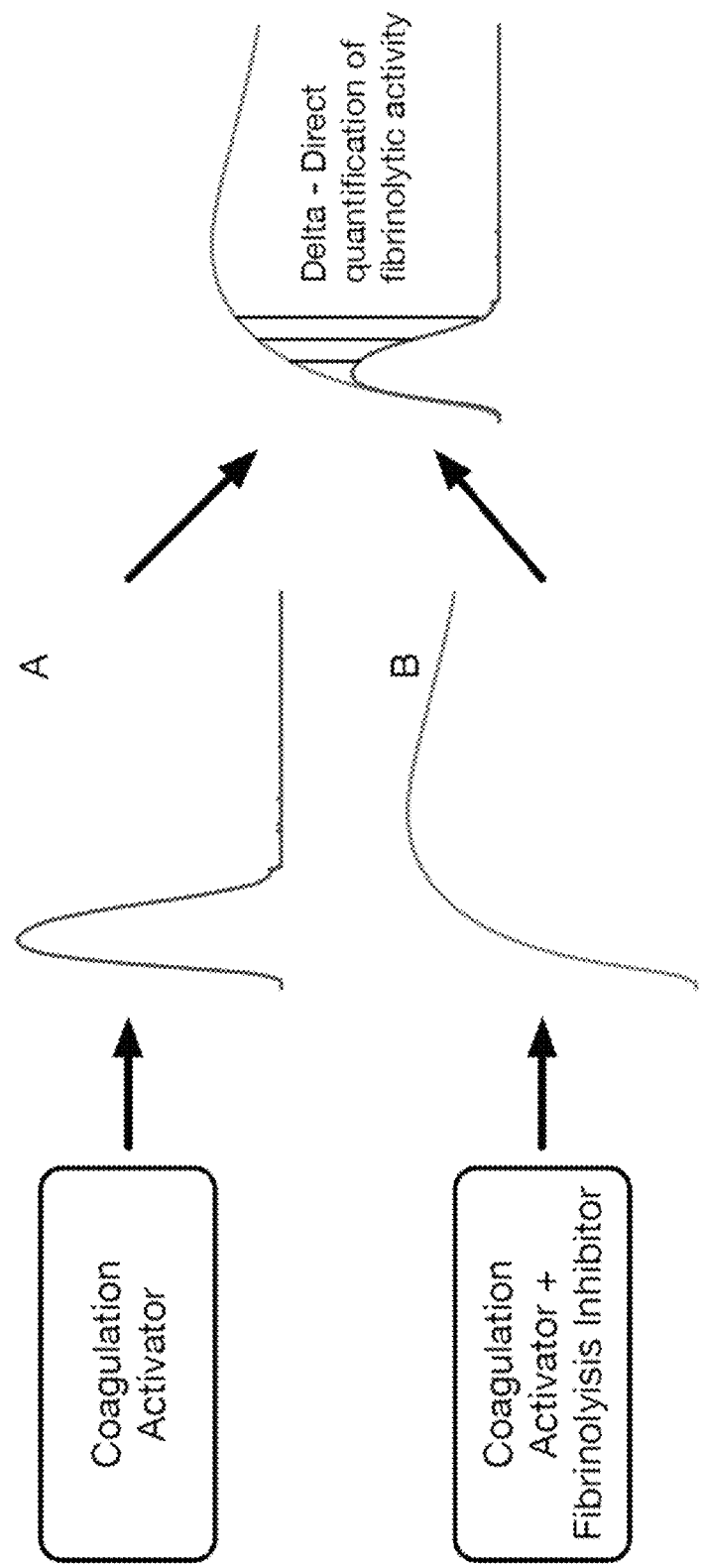
FIG. 14 shows an example of shear modulus curves obtained with an activator of coagulation and with and without a fibrinolysis inhibitor. A differential comparison of these curves can provide information about the fibrinolytic activity of the sample.
Figure 15:
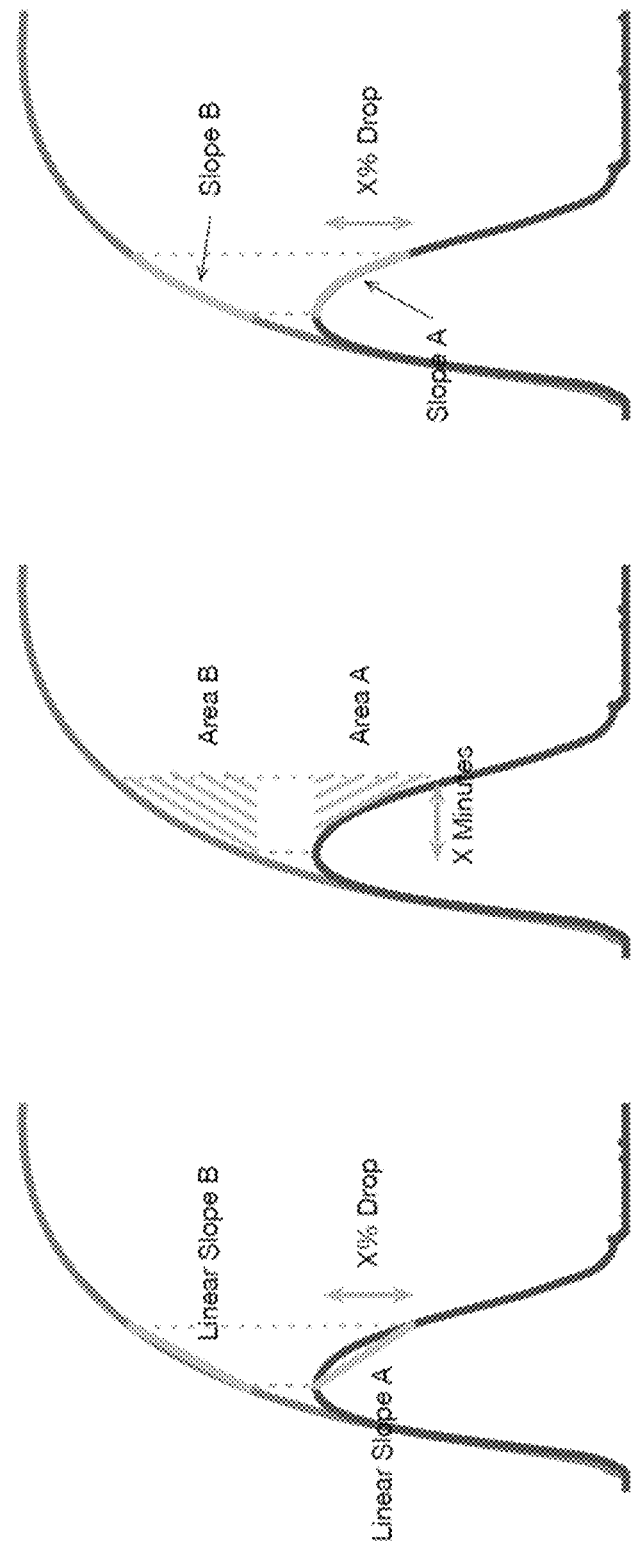
FIG. 15 shows potential embodiments of differential metrics that can be measured from shear modulus curves obtained with an activator of coagulation and with and without a fibrinolysis inhibitor.

In some embodiments, clot time and clot stiffness are measured by analyzing a shear modulus (clot stiffness) versus time curve that is generated within each measurement channel in the cartridge. FIG. 13 shows an example shear module versus time curve, in accordance with an illustrative embodiment. Clot time may be determined by identifying when the clot stiffness meets or exceeds a threshold value, or when the first or higher derivative of such property being measured meets or exceeds a threshold value, or at the point of maximum acceleration in the rate of clot stiffness, or some combination of the above methods. Clot stiffness may be estimated by the clot stiffness at a fixed time after clot time, or the maximum overall clot stiffness measured within some time limit, or the clot stiffness at the point of maximum rate of change in clot stiffness, or some combination of the above methods. Similar methods can also be applied to measure the effects of fibrinolysis (i.e., clot dissolution) and the corresponding reduction in clot stiffness. In some embodiments, clot stiffness changes can be calculated as percentage drop in clot stiffness over a fixed time window, as a rate of change of clot stiffness over time, as area under or over the clot stiffness vs time curve within a predefined time window, as the time required to achieve a predefined drop in clot stiffness, or combinations thereof. Similar curves and similar measurements to those just described can be formed by plotting the Young's modulus, viscosity, or other viscoelastic property of the sample being measured.

TABLE 3

Parameters reported from measurement of the preferred embodiments discussed in relation to Table 1.

| Hemostatic Index | Units | Description | Measurement |
|---|---|---|---|
| Clot Time | Minutes (min) | Clot time in citrated whole blood | Clot time measured from channel #1 with kaolin activation (intrinsic pathway) |
| Heparinase Clot Time | Minutes (min) | Clot time in citrated whole blood with heparin neutralization | Clot time measured from channel #2 with kaolin activation and heparinase I |
| Clot Stiffness | hecto Pascals (hPa) | Stiffness of the whole blood clot | Clot stiffness measured from channel #3 with thromboplastin activation (extrinsic pathway) and polybrene |
| Fibrinogen Contribution | hecto Pascals (hPa) | Contribution of functional fibrinogen to clot stiffness | Clot stiffness measured from channel#4 with thromboplastin activation, polybrene, and abciximab |
| Clot Time Ratio | Unit less | Assessment of residual heparin anticoagulation | Calculated ratio of clot time values from channels #1 and #2 |
| Platelet Contribution | hecto Pascals (hPa) | Contribution of platelet activity to clot stiffness | Calculated from subtraction of the clot stiffness values from channels #3 and #4 |

A person of ordinary skills in the art should recognize that clot time and clot stiffness can be estimated using a number of methodologies and criteria. Clot times and clot stiffness values obtained from the, at least, four channels/measurements may be combined to provide, at least, six parameters can depict a functional status of the patient's hemostatic system. The indexes are summarized in Table 3. Relationship between results (clot time, clot stiffness, clot stiffness change, etc.) from different channels may be verified to be within expected ranges as additional quality control checks to verify instrument, cartridge, and sample function.

In other embodiments, other reagents can be used and other hemostatic indexes or output parameters can be obtained such as in the case of a fibrinolytic index, indexes corresponding to the functionality of anti-platelet treatments, indexes corresponding to the functionality of anti-coagulation treatments, etc.

For example, one or more fibrinolysis indexes could be formed using the clot stiffness changes measured in any of the channels presented in Table 2, but preferably channels #3 and #4. Alternatively, a fibrinolysis index could be formed by differential combination of the clot stiffness changes measured in channels #2 and channel #3 presented in Table 2. Such combination could be in the form of a ratio, a difference, or combinations thereof. One of the benefit of using a combination of clot stiffness changes measured with and without an anti-fibrinoltyic reagent is the ability to mitigate the interfering effects of non-fibrinolysis driven reductions in clot stiffness values. In some embodiments, TXA or other fibrinolysis inhibitor reagent can be included in both channel #2 and channel #4 of the example cartridge of Table 2. With such modifications the parameters Clot Stiffness, Platelet Contribution, and Fibrinogen Contribution could be derived without the influence of fibrinolysis by combination of the clot stiffness measurements obtained in channel #2 and channel #4.

As discussed above, an example user interface is described in commonly assigned U.S. Pub. No. 2011/0252352 to Viola et al., which is incorporated by reference herein in its entirety. The example user interface may be used to display the measured hemostatic indexes as discussed in relation to Table 4, among other parameters.

TABLE 4

Parameters reported from measurement of the preferred embodiments discussed in relation to Table 2.

| Hemostatic index | Units | Description | Measurement |
|---|---|---|---|
| Clot Time | Minutes (min) | Clot time in citrated whole blood | Clot time measured from channel #1 with kaolin activation (intrinsic pathway) |
| Clot Stiffness | hecto Pascals (hPa) | Stiffness of the whole blood clot | Clot stiffness measured from channel #3 with thromboplastin activation (extrinsic pathway) and polybrene |
| Fibrinogen Contribution | hecto Pascals (hPa) | Contribution of functional fibrinogen to clot stiffness | Clot stiffness measured from channel #4 with thromboplastin activation, polybrene, and abciximab |
| Platelet Contribution | hecto Pascals (hPa) | Contribution of platelet activity to clot stiffness | Calculated from subtraction of the clot stiffness values from channels #3 and #4 |
| Clot Stiffness Change | % or hPa/sec or sec | Clot stiffness change over time | Changes (% or rate of change) in clot stiffness measured from channels #2 and #3 |
| Clot Reduction Differential | % or hPa/sec, or no units | Differential rate of clot stiffness changes with and without anti-fibrinolytic | Differential comparison of clot stiffness change measured in channels #2 and #3. |

As noted before, in various embodiments, the testing chambers 16 are shaped to facilitate ultrasound testing of viscoelastic properties of the sample, but alternative geometries can also be implemented to facilitate other types of testing. Such an ultrasound testing system is described in commonly assigned U.S. Pat. No. 9,726,647 and U.S. Pub. No. 2016/0139159, both of which are hereby incorporated by reference in their entirety. Ultrasound transducers in the measuring system connect with the testing chambers 16 of the cartridge 100 via compliant and deformable elastomers 21 which are affixed to a testing block 21d on the cartridge 100.

Figure 9:
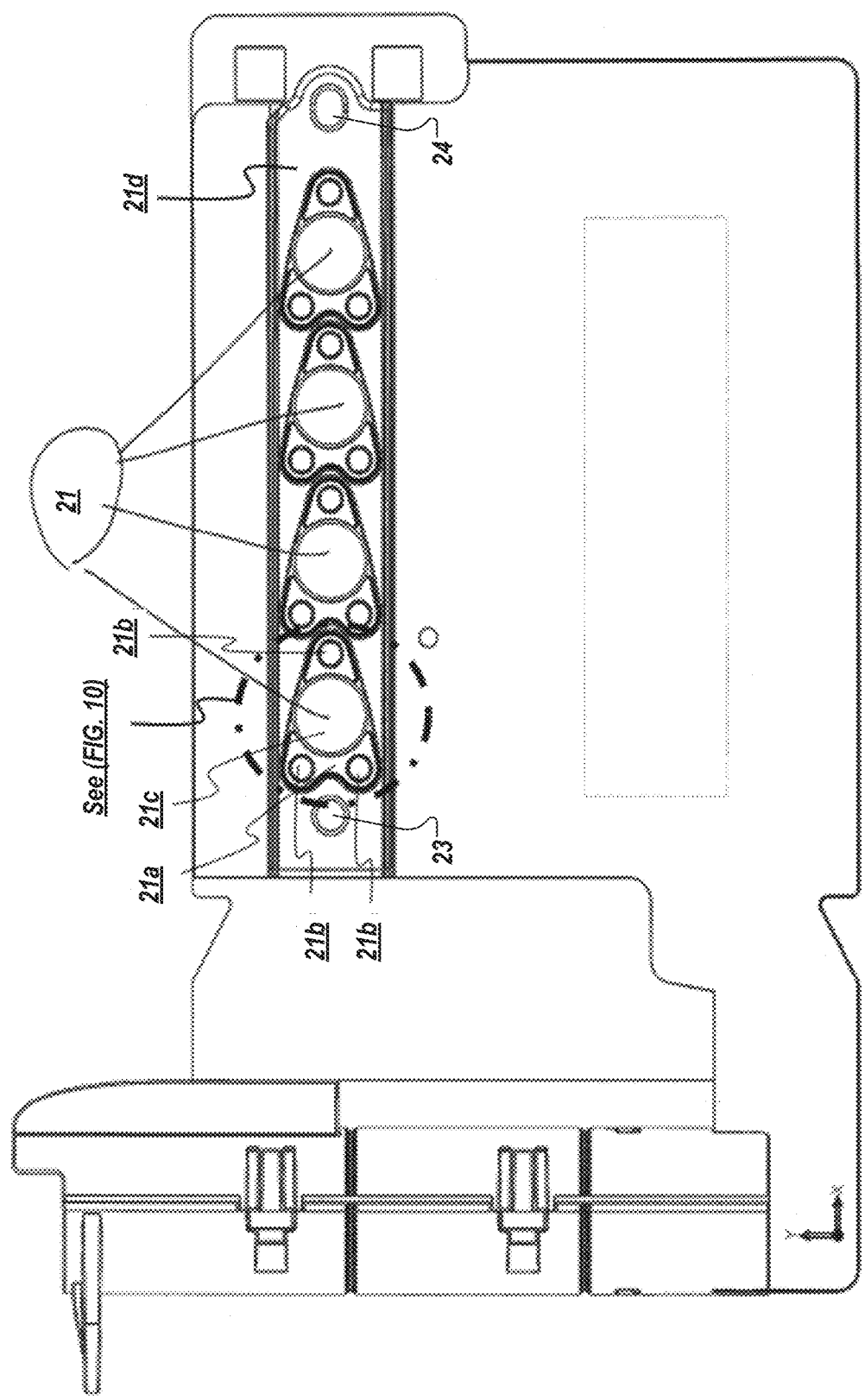
FIG. 9 shows an example testing chamber section for use with the example cartridge, in accordance with an illustrative embodiment.

Example elastomeric materials optionally include, Dynaflex D3202, Versaflex OM 9-802CL, Maxelast 54740, RTP 6035, Versaflex CL2003X, among others. Referring now to FIG. 9 unless indicated otherwise, the testing block 21d is aligned with the testing chambers 16 (see FIG. 5B) via alignment slots 23 and 24 on the cartridge 100. Referring still to FIG. 9, the elastomers 21 may be affixed to the testing block 21d via a flange 21a on the elastomers 21. The flange 21a may have a plurality of alignment holes 21b that may receive corresponding alignment pegs (not shown) from the testing block 21d. The soft elastomers 21 may also each include a lens 21c that focuses ultrasound energy within the sample at the testing chambers 16.

Figure 16:
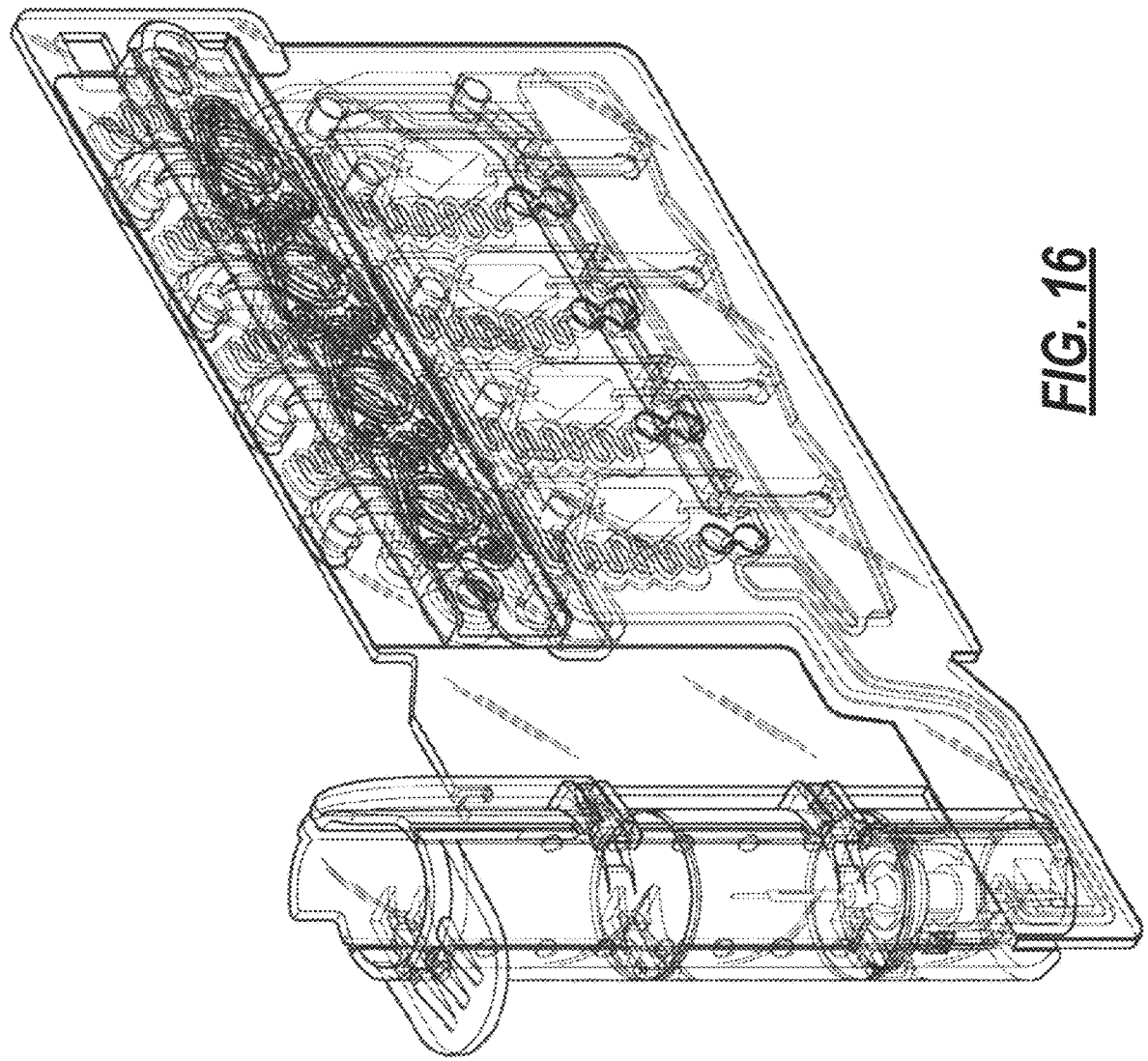
FIG. 16 shows a photograph of an exemplary cartridge of FIGS. 1, 2, 3, 4, 5A, 5B, 7, 8, and 9 for use in a disposable system, in accordance with an illustrative embodiment.
Figure 17:
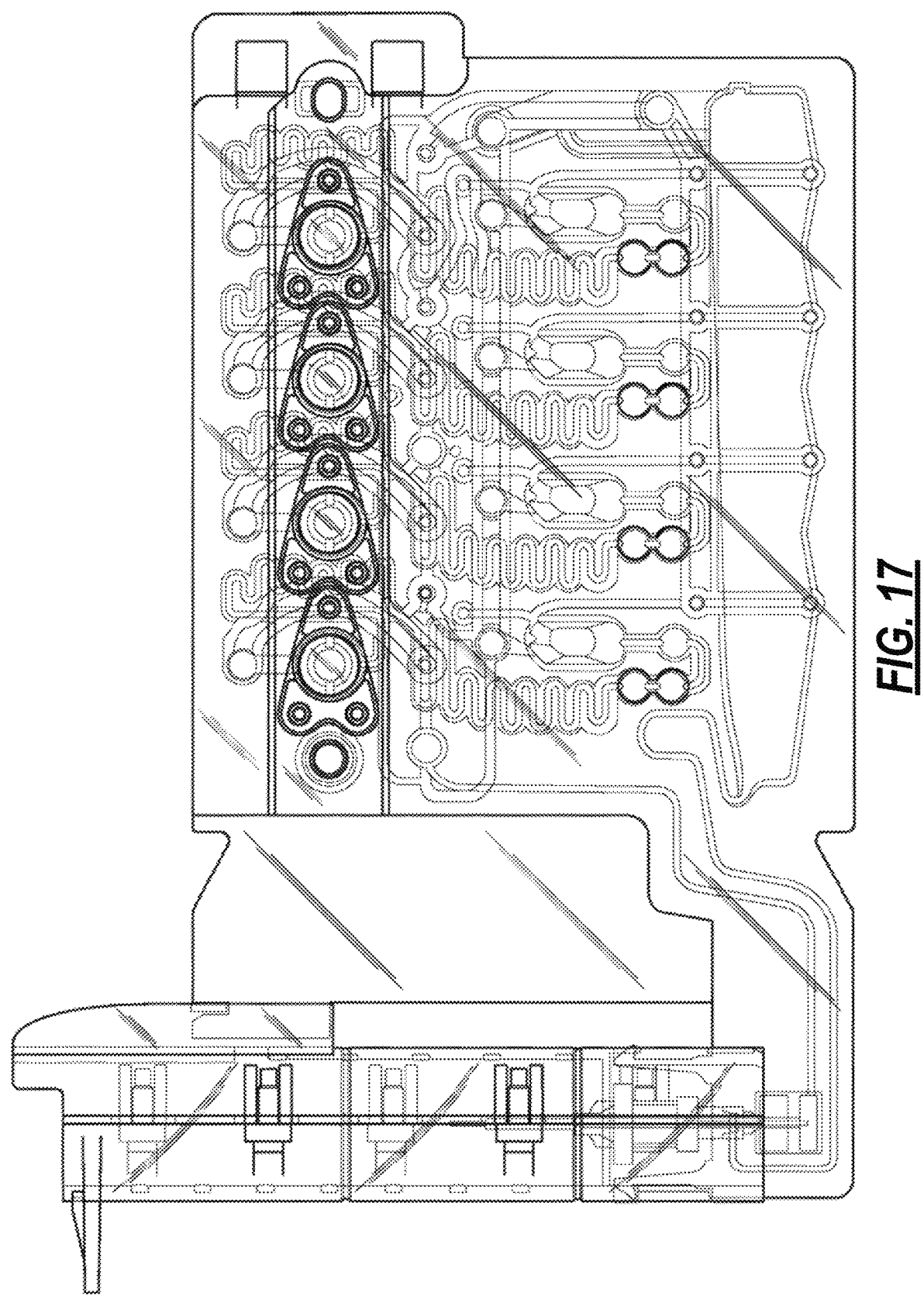
FIG. 17 shows a front view of the exemplary cartridge of FIGS. 1, 2, 3, 4, 5A, 5B, 7, 8, and 9 in accordance with an illustrative embodiment.
Figure 18:
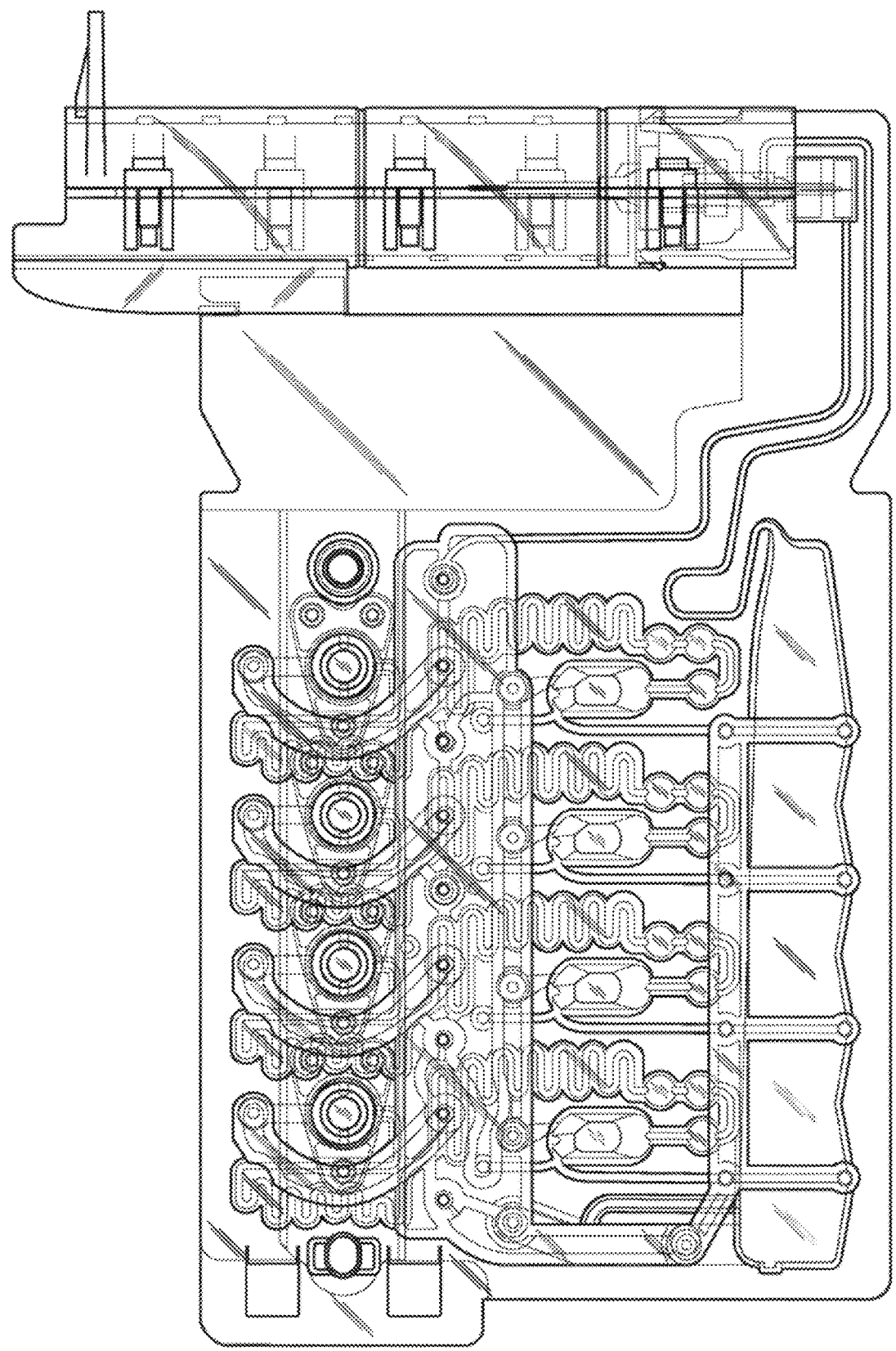
FIG. 18 shows a front view of the exemplary cartridge of FIGS. 1, 2, 3, 4, 5A, 5B, 7, 8, and 9, in accordance with an illustrative embodiments.

FIG. 16 shows a photograph of an exemplary cartridge of FIGS. 1, 2, 3, 4, 5A, 5B, 7, 8, and 9 for use in a disposable system, in accordance with an illustrative embodiment. FIG. 17 shows a front view of the exemplary cartridge of FIGS. 1, 2, 3, 4, 5A, 5B, 7, 8, and 9, in accordance with an illustrative embodiment. FIG. 18 shows a front view of the exemplary cartridge of FIGS. 1, 2, 3, 4, 5A, 5B, 7, 8, and 9, in accordance with an illustrative embodiments.

Figure 10:
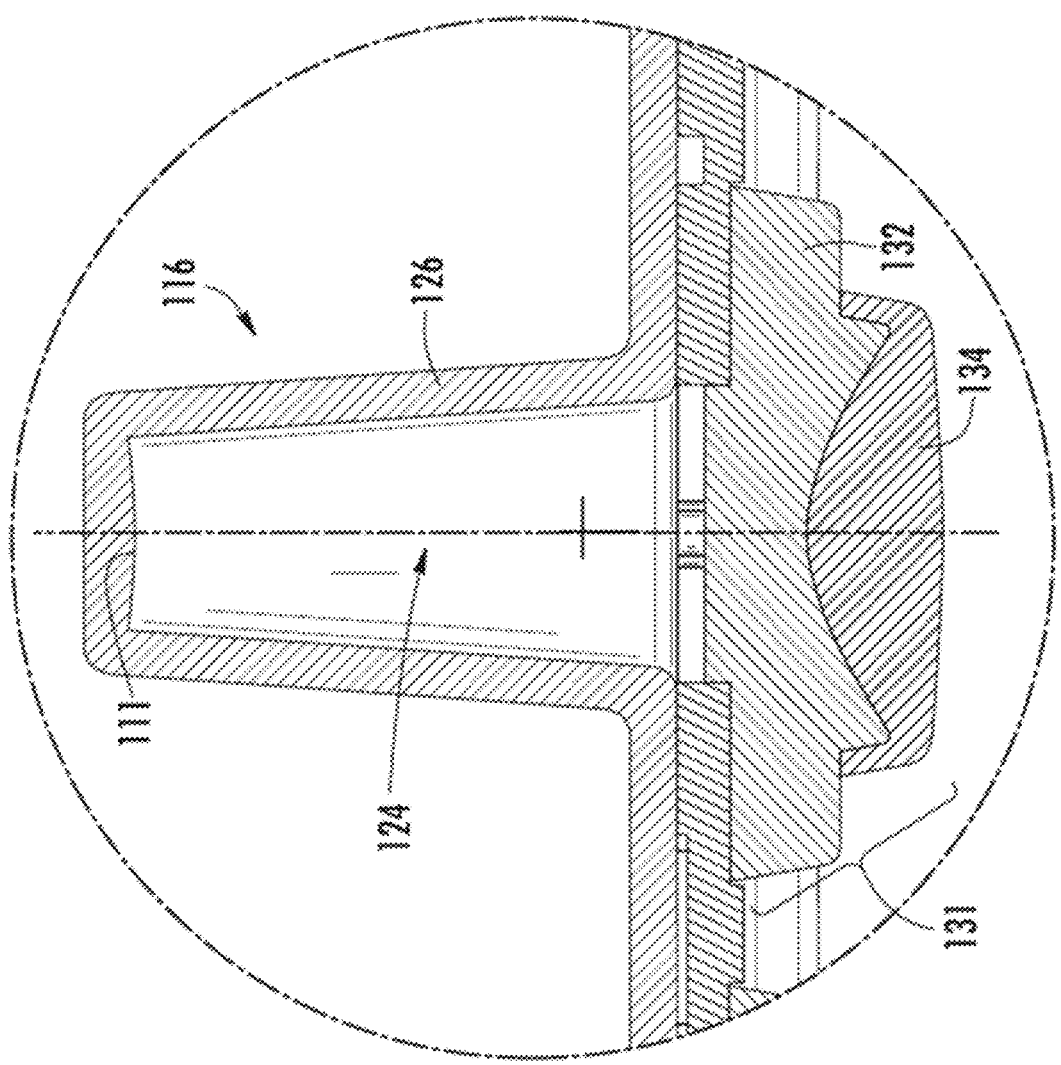
FIG. 10 shows a cross-sectional view of an example testing chamber in the example testing chamber section, in accordance with an illustrative embodiment.
Figure 11:
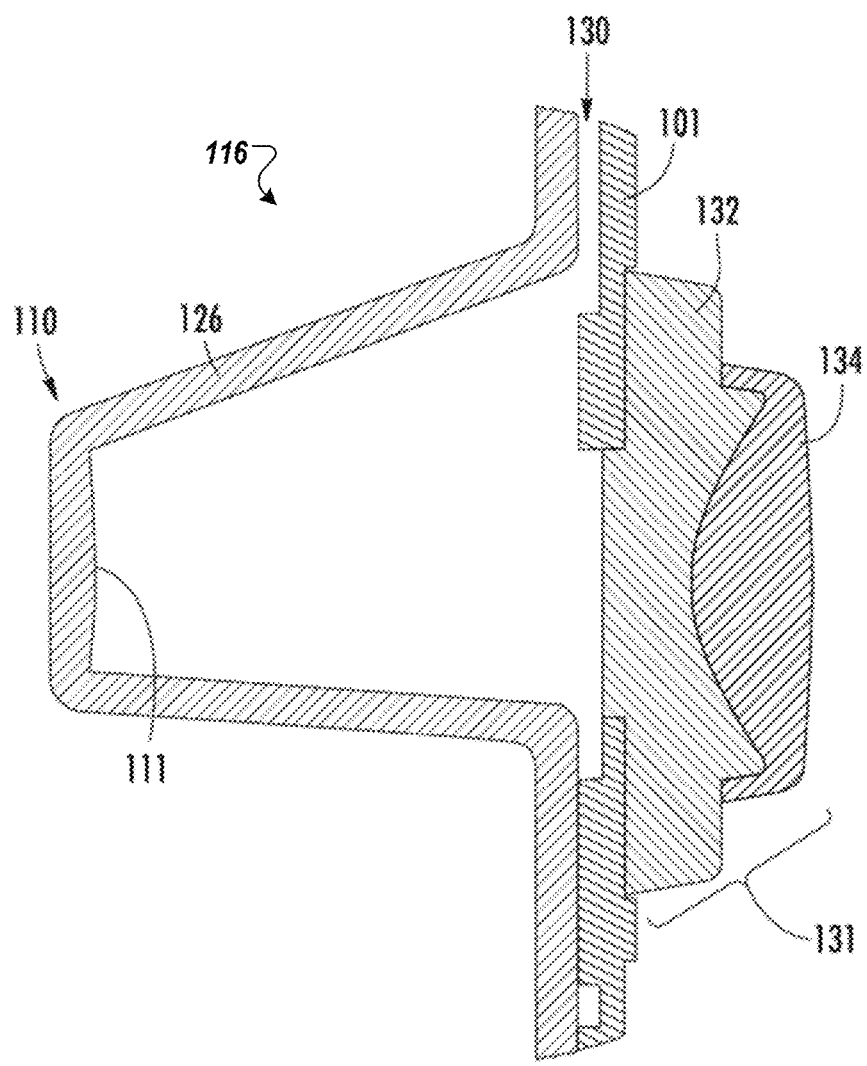
FIG. 11 shows a detailed cross-sectional view of the example testing chamber of FIG. 10, in accordance with an illustrative embodiment.
Figure 12:
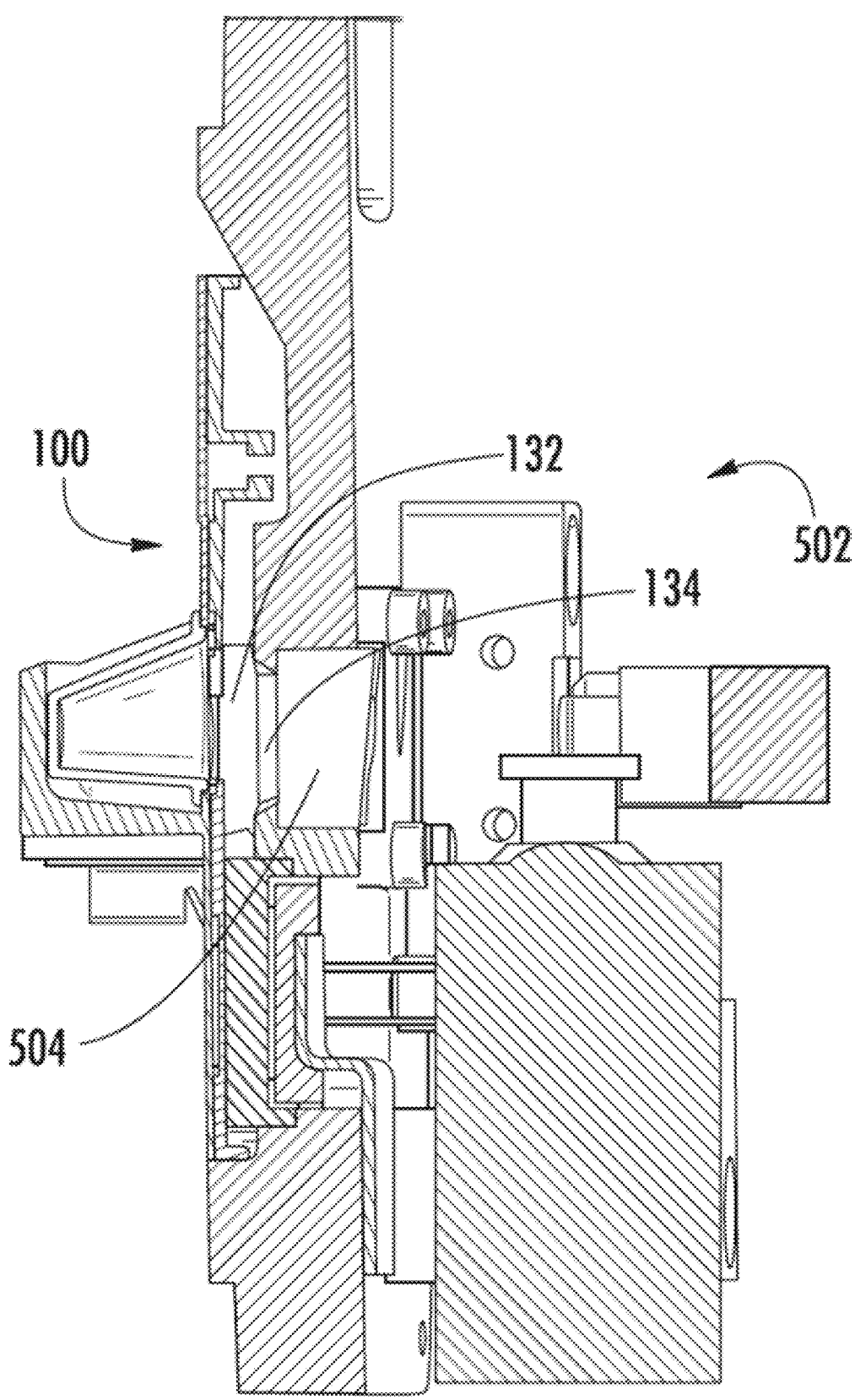
FIG. 12 shows a cross-sectional view of the disposable system operatively coupled to a measurement system, in accordance with an illustrative embodiment.

As described in U.S. Pat. No. 9,272,280, which is incorporated by reference herein in its entirety, in various embodiments, the consumable cartridge contains a lens assembly that focuses ultrasound energy within the sample that can be used to generate streaming and mixing. The lens assembly, or sound focusing assembly, is designed using a soft material, such as a thermoplastic elastomer 134 (previously referred to as 21), in conjunction with a rigid substrate 132 (e.g., formed of testing block 21d), such as polystyrene as shown in FIGS. 10, 11, and 12. This combination provides a dry ultrasound coupling that does not require the use of any fluid or gel couplant. Note that the same lens and ultrasound driver used for hemostasis measurement can be used in this matter to provide mixing. Increasing acoustic energy for mixing can be delivered by, for example, increasing pulse length, pulse amplitude or pulse repetition frequency.

Referring now to FIG. 10, a top cross-sectional view of the testing chamber 116 (referred to previously as testing chamber 16) is shown. To seal each test chamber, e.g. test chamber 116, a lens assembly 131 includes a rigid substrate 132 and a couplant 134 that can be positioned at the back end of each test chamber.

Referring still to FIG. 10, each couplant 134 comprises an elastomeric material. Optionally, the elastomeric material is a thermoplastic elastomer (TPE). Example elastomeric materials optionally include, Dynaflex D3202, Versaflex OM 9-802CL, Maxelast 54740, RTP 6035, Versaflex CL2003X, among others. Optionally the couplant is overmolded to the rigid substrate. Optionally the couplant is mechanically anchored to the rigid substrate.

Referring still to FIG. 10, between each couplant 134 and the open space of each test chamber is a rigid substrate 132. The rigid substrate and the couplant form an interface that focuses ultrasound transmitted (e.g. lens assembly) by an ultrasonic transducer into the chamber's open space and onto any biological fluid and/or reagents in the chamber. The rigid substrate of the lens can comprise a material which allows sound to pass and that can act to focus ultrasound at some level within the space. Optionally, the rigid substrate comprises a styrene.

Referring now to FIG. 11, The lens assembly may be glued or welded to the surface 101 of the testing block 21d (shown in FIG. 11 as element 132) to secure the lens in place in an orientation that allows the desired focusing of sound. Alternatively, the lens assembly is optionally manufactured together with the surface 101 of the testing block 21d. In this regard, the rigid substrate 132 can be molded with the surface 101 of the testing block 21d and the couplant 134 can be overmolded or mechanically anchored on the rigid substrate. A wide variety of materials can be used to construct the device. For example, plastics can be used for single use, disposable cartridges.

Referring still to FIG. 11, each of the test chambers 116 can have a lens assembly positioned over the large opening of each chamber's open space. In this way, each chamber can be separately interrogated by focused ultrasound.

Referring still to FIG. 11, when placed in the instrument, the couplant 134 can be placed in acoustic communication with a transducer for supplying ultrasound through the lens assembly and into a test chamber 116. Optionally, an intermediate layer of an acoustically permeable material is positioned between an ultrasonic transducer and the couplant. For example, and intermediate layer or block of Rexolite® or TPX® can be used. The intermediate layer can be forced against the couplant and can be in acoustic contact with the transducer.

Referring still to FIG. 11, sound generated by a transducer passes through the intermediate layer, through the couplant, through the rigid substrate, and is focused within the biological sample, such as blood, and reagent in the test chamber. Some of the sound directed into chamber contacts the distal interior surface 111 of the test chamber, which is defined by the surface 126. Optionally, the surface is polystyrene. The distal interior surface has a known geometry and is positioned at a known distance from the ultrasound source. The distal interior surface 111 is used as a calibrated reflector, which is used to estimate the speed of sound and attenuation of sound in a test chamber at base line and during the process of clot formation and clot dissolution. These measurements can be used, for example, to estimate hematocrit of the subject along with the indexes of hemostasis. The sound generated by the transducer can be focused within the biological sample in a test chamber using a parabolic mirror that is coupled to the biological sample using an elastomer.

Other example cartridge apparatus and measurement system, and methods thereof, are described in U.S. Pat. No. 9,031,701; U.S. Provisional Appl. No. 61/443,084; U.S. Pat. Nos. 9,272,280; 9,410,971; U.S. Provisional Appl. No. 61/443,088; U.S. Publication No. 2011/0252352; published PCT Publication No. WO2011/127436; U.S. Publication No. 2012/0294767; U.S. Pat. Nos. 7,892,188; 8,740,818; and U.S. Publication No. 2016/0274067, each of which is incorporated by reference herein in its entirety.

As noted, the cartridge and features described herein can be modified for use with other types of measurement systems such as thromboelastography-based systems, thromboelastometry-based systems, optical-based systems, fluorescence-based systems, colorimetric-based systems, aggregometry-based systems, resonance-based system, and an electrical impedance-based system, among others.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used in the claims, the term "first", "second", and "third" are provided merely as labels and do not intended to connote a sequence.

What is claimed is:

1. A method comprising:
   receiving in a cartridge a sample from a sample holding tube;
   metering the sample in a plurality of metering chambers to form a plurality of metered samples;
   mixing each of the plurality of metered samples with a respective set of one or more reagents, or combinations of reagents, to form a respective mixed sample, wherein a first metered sample of the plurality of metered samples is mixed with a first set of one or more reagents or a combination of reagents to form a first mixed sample by repeatedly flowing, over a plurality of repeated cycles, the first metered sample (i) in a first direction along a mixing path defined (a) along a first metering chamber, (b) through a first set of one or more reagent pockets with the first set of one or more reagents or the combination of reagents located therein, and (c) along a first serpentine pathway in communication with the first metering chamber and the first set of one or more reagent pockets, until at least a portion of the first metered sample reaches a first detection zone located in, or after, the first serpentine pathway and (ii) in a second direction reversed to the first direction from the first detection zone through at least a portion of the first serpentine pathway toward the first metering chamber, wherein the first metering chamber is connected to a first testing chamber through the first serpentine pathway and the first set of one or more reagent pockets, and wherein the first metered sample is repeatedly flowing in the first and second direction over the mixing path from an application of a varying pressure from a measurement system at a first port in communication with the first serpentine pathway;

driving the first mixed sample into the first testing chamber; and interrogating the first testing chamber by the measurement system to determine one or more viscoelastic properties of the first mixed sample, wherein the determined one or more viscoelastic properties of the first mixed sample is provided for an assessment of hemostasis of the sample.

2. The method of claim 1, further comprising:

receiving the sample in a heating chamber configured to adjust a temperature of the sample from a first temperature to a second temperature, wherein the second temperature is different from the first temperature and associated with body temperature, and wherein the first metered sample is received from the heating chamber.

3. The method of claim 2, wherein the sample is moved into the heating chamber in response to a first applied positive or negative pressure that is applied by, or generated from, the measurement system.

4. The method of claim 2 further comprising:

conditioning the sample in the heating chamber, wherein the first metered sample is mixed with the first set of one or more reagents following exit from the first metering chamber.

5. The method of claim 4, further comprising:

isolating the first metered sample in the first metering chamber to prevent the first metered sample from contacting the first set of one or more reagents during the filling of the first metering chamber.

6. The method of claim 1, wherein the step of flowing the first metered sample comprises:

applying a first positive or negative pressure from the measurement system at the first port in communication with the first serpentine pathway to move the first metered sample through the first serpentine pathway in the first direction; and applying a second positive or negative pressure that is opposite to the first positive or negative pressure from the measurement system to move the first metered sample through the first serpentine pathway in the second direction.

7. The method of claim 1, wherein the step of receiving the first mixed sample in the first testing chamber comprises:

applying a negative or differential pressure via a second port, wherein the second port is in fluid communication with the first testing chamber.

8. The method of claim 7, wherein the first testing chamber is located downstream of the first serpentine pathway and the second port is located downstream of the first testing chamber.

9. The method of claim 1, wherein the first set of one or more reagent pockets includes the first set of one or more reagents, or the combination of reagents, wherein the first set of one or more reagents, or the combination of reagents, is in the form of one or more lyophilized beads.

10. The method of claim 9, wherein the first set of one or more reagent pockets associated with the first testing chamber comprises kaolin, calcium, buffers, and stabilizers, wherein the first testing chamber forms a part of a first test channel of the cartridge.

11. The method of claim 9, wherein a second set of one or more reagent pockets associated with a second test chamber comprises:

a combination of kaolin, heparinase I, calcium, buffers and stabilizers; or a combination of thromboplastin, polybrene, calcium buffers, and stabilizers, wherein the second testing chamber forms a part of a second test channel of the cartridge.

12. The method of claim 9, wherein a third set of one or more reagent pockets associated with a third test chamber, comprises thromboplastin, polybrene, calcium, buffers, and stabilizers, wherein the third testing chamber forms a part of a third test channel of the cartridge.

13. The method of claim 9, wherein a third set of one or more reagent pockets associated with a third test chamber as a third test channel of the cartridge comprises thromboplastin, polybrene, at least one of abciximab and cytochalasin D, calcium, buffers, and stabilizers.

14. The method of claim 1, wherein the measurement system is configured to determine at least one of:

a clot time-of the first mixed sample, a clot stiffness or a heparinase clot time of a second mixed sample, and a fibrinogen contribution of a third mixed sample.

15. The method of claim 1, wherein the measurement system is configured to determine:

a clot stiffness, a clot stiffness change, and a clot reduction differential of the first mixed sample.

16. The method of claim 1, wherein the measurement system is configured to determine shear modulus of the first mixed sample as the determined one or more viscoelastic properties of the first mixed sample.

17. The method of claim 1, wherein the measurement system is configured to determine viscoelastic properties of a second mixed sample.

18. The method of claim 17, wherein the measurement system is configured to determine viscoelasticity properties of a third mixed sample.

19. The method of claim 1, wherein the first set of one or more reagent pockets associated with the first testing chamber comprises a coagulation activator selected from the group consisting of kaolin, Hageman factor, celite, glass, ellagic acid, micronized silica, tissue factor, recombinant tissue factor, thromboplastin, thrombin, factor Xa, reptilase, ecarin, and Russell's viper venom.

20. The method of claim 1, wherein a second set of one or more reagent pockets associated with a second test chamber comprises a platelet activator or inhibitor selected from the group consisting of abciximab, eptifibatide, tirofiban, roxifiban, orbofiban, cytochalasin D, blebbistatin, PAR1 inhibitors, PAR4 inhibitors, glycoprotein I.B. inhibitors, thrombin receptor activating peptide (TRAP), adenosine diphosphate (A.D.P.), and arachidonic acid.

21. The method of claim 1, wherein a third set of one or more reagent pockets associated with a third test chamber comprises a fibrinolytic function activator or inhibitor selected from the group consisting of tPA, uKA, streptokinase, TAFIa, plasmin/plasminogen, aprotinin, epsilon-aminocaproic acid, tranexamic acid, plasminogen activator inhibitor 1 (PAI1), α2-antiplasmin (α2-AP), plasmin-antiplasmin complexes, and carboxypeptidase inhibitor.

22. The method of claim 1, wherein a fourth set of one or more reagent pockets associated with a fourth test chamber comprises a reagent selected from the group consisting of FXIIIa inhibitor, Hexadimethrine bromide (polybrene), heparinase, ristocetin, heparin, low molecular weight heparin, corn trypsin inhibitor, adenosine, GPRP, calcium, fibronectin, collagen, epinephrine, immuno-detection reagent, direct thrombin inhibitor, factor Xa inhibitor, direct thrombin inhibitor, and thrombomodulin.

* * * * *